US011080369B2

(12) United States Patent
Lei et al.

(10) Patent No.: US 11,080,369 B2
(45) Date of Patent: Aug. 3, 2021

(54) ENTERPRISE-LEVEL LICENSING FOR A BARCODE DECODER WITHIN A MOBILE DEVICE APPLICATION

(71) Applicant: The Code Corporation, Draper, UT (US)

(72) Inventors: Ming Lei, Taylorsville, NJ (US); David Bubnoski, Marlton, NJ (US)

(73) Assignee: The Code Corporation, Murray, UT (US)

( * ) Notice: Subject to any disclaimer, the term of this patent is extended or adjusted under 35 U.S.C. 154(b) by 379 days.

(21) Appl. No.: 16/112,413

(22) Filed: Aug. 24, 2018

(65) Prior Publication Data

US 2020/0065454 A1     Feb. 27, 2020

(51) Int. Cl.
| | |
|---|---|
| *G06F 21/00* | (2013.01) |
| *G06F 21/10* | (2013.01) |
| *G06F 8/61* | (2018.01) |
| *G16H 40/20* | (2018.01) |
| *G06K 7/14* | (2006.01) |
| *G06K 7/10* | (2006.01) |

(52) U.S. Cl.
CPC .............. *G06F 21/105* (2013.01); *G06F 8/61* (2013.01); *G06K 7/1413* (2013.01); *G16H 40/20* (2018.01); *G06F 2221/0753* (2013.01); *G06K 2007/10524* (2013.01)

(58) Field of Classification Search
CPC .......... G06F 21/105; G06F 21/10; G06F 8/61; G06F 2221/0753; G16H 40/20; G06K 7/1413; G06K 2007/10524
See application file for complete search history.

(56) References Cited

U.S. PATENT DOCUMENTS

| | | | |
|---|---|---|---|
| 2009/0055320 A1* | 2/2009 | Goertier ............. | G06Q 20/1235 705/59 |
| 2014/0282610 A1* | 9/2014 | Strom ...................... | G06F 21/12 719/313 |
| 2016/0188932 A1* | 6/2016 | Powell .................. | G06K 7/0004 235/462.42 |

\* cited by examiner

*Primary Examiner* — Yogesh Paliwal
(74) *Attorney, Agent, or Firm* — Timothy P. O'Hagen; Ray Quinney & Nebeker

(57) ABSTRACT

An application on a mobile device may include a barcode decoder. The application may be configured to download a configuration file. The configuration file may include an enterprise identifier that is uniquely associated with an enterprise. The application may additionally be configured to obtain a license key for the barcode decoder. The license key may be based on the enterprise identifier. The application may additionally be configured to transition the barcode decoder from an inactive state to an active state conditional upon verifying that the license key is based on the enterprise identifier.

20 Claims, 16 Drawing Sheets

502 {
  License Key
  　　Symbologies: A, B, C ~ 508
  　　Lease Term: Date, Time ~ 510
  　　Enterprise ID ~ 516
}

504 {
  License Key
  　　Symbology: A ~ 512a
  　　　　Qty.: Unlimited ~ 514a
  　　Symbology: B ~ 512b
  　　　　Qty.: XX ~ 514b
  　　Symbology: C ~ 512c
  　　　　Qty.: XX ~ 514c
  　　Lease Term: Date, Time ~ 515
  　　Enterprise ID ~ 516
}

506 {
  License Key
  　　Symbology: A ~ 518a
  　　　　Term: Perpetual ~ 520a
  　　　　Qty.: Unlimited ~ 522a
  　　Symbology: B ~ 518b
  　　　　Term: Perpetual ~ 520b
  　　　　Qty.: XX ~ 522b
  　　Symbology: C ~ 518c
  　　　　Term: Date, Time ~ 520c
  　　　　Qty.: XX ~ 522c
  　　Enterprise ID ~ 516
}

FIG. 5

Group ID ～ 740
    License ID ～ 742
        Qty. Purchased : XX ～ 744
        Qty. Used     : YY ～ 746
        Qty. Remaining : ZZ ～ 748

Group ID ～ 750
    License ID ～ 752a
        Qty. Purchased : Unlimited ～ 754a
        Qty. In Use     : N/A ～ 756a
        Qty. Remaining : N/A ～ 758a
    License ID ～ 752b
        Qty. Purchased : XX ～ 754b
        Qty. In Use     : YY
        Qty. Remaining : ZZ 756b
758b

| ID | Expire |
|---|---|
| 1 | MM/DD |
| 2 | MM/DD |
| 3 | MM/DD |
| 4 | MM/DD |
| 5 | MM/DD |
| 6 | MM/DD |
| 7 | MM/DD |
| 8 | MM/DD |

FIG. 6C

ENTERPRISE-LEVEL LICENSING FOR A BARCODE DECODER WITHIN A MOBILE DEVICE APPLICATION

BACKGROUND

Smartphones and other types of portable hand-held computing devices, such as tablet computers, are in widespread use today, most often in connection with entertainment, communications and office productivity. Most smartphones include a camera, and applications have been developed for using the camera to read barcodes. In a typical known application an image feed from the camera is displayed on the display screen of the smartphone.

SUMMARY

In accordance with an aspect of the present disclosure, a mobile device is disclosed that includes one or more processors, memory, and an application stored in the memory of the mobile device. The memory may be in electronic communication with the one or more processors. The application may include a barcode decoder. The application may be executable by the one or more processors to download a configuration file. The configuration file may include an enterprise identifier that is uniquely associated with an enterprise. The application may additionally be executable by the one or more processors to obtain a license key for the barcode decoder. The license key may be based on the enterprise identifier. The application may additionally be executable by the one or more processors to transition the barcode decoder from an inactive state to an active state conditional upon verifying that the license key is based on the enterprise identifier.

The configuration file may be downloaded from a workflow server. Communication between the application and the workflow server may occur via a mobile application server and may be based on the enterprise identifier.

The memory may further include instructions that are executable by the one or more processors to download the application from an application download server and install the application. The barcode decoder may be in the inactive state when the application is installed.

The license key may include the enterprise identifier. Verifying that the license key is based on the enterprise identifier may include verifying that the enterprise identifier within the license key matches the enterprise identifier within the configuration file.

In some implementations, the license key may be obtained from the workflow server. The configuration file may include the license key. In some implementations, the license key may be obtained from a license server that is distinct from the workflow server.

The application may include barcode reading functionality. The application may also include other functionality in addition to the barcode reading functionality.

In some implementations, the workflow server may be managed by a hospital information system (HIS) vendor. The enterprise may include a hospital. The enterprise identifier may include a hospital identifier. The HIS vendor may assign the hospital identifier to the hospital.

In accordance with another aspect of the present disclosure, a method for enterprise-level licensing is disclosed. The method includes sending a configuration file to an application running on a mobile device. A user of the mobile device may be associated with an enterprise. The configuration file may include an enterprise identifier that is uniquely associated with the enterprise. The method may also include obtaining a license key for the enterprise. The license key may enable use of a barcode decoder within the mobile device application. The license key may be based on the enterprise identifier. The method may also include sending the license key to the application.

The method may additionally include creating the configuration file. The configuration file may include at least one of a mobile device identifier that is uniquely associated with the mobile device, or a user identifier that is uniquely associated with a user of the mobile device.

The method may additionally include determining whether the enterprise has purchased a license to use the barcode decoder. The license key may be sent to the application conditional upon determining that the enterprise has purchased the license.

In some implementations, obtaining the license key may include receiving the license key from a supplier of the barcode decoder. In some implementations, the configuration file may include the license key.

In some implementations, the method may be implemented by a hospital information system (HIS) vendor. The enterprise may include a hospital. The enterprise identifier may include a hospital identifier. The configuration file may be sent to the application in response to receiving a request for access to health care records maintained by the HIS vendor and receiving information identifying the hospital.

In accordance with another aspect of the present disclosure, a method for enterprise-level licensing may include providing a barcode decoder for a mobile device application. The mobile device application may be usable by a plurality of different enterprises. The method may include creating a license key for an enterprise that has purchased a license to use the barcode decoder. The license key may enable use of the barcode decoder. The license key may be based on an enterprise identifier that is uniquely associated with the enterprise. In some implementations, the license key may include the enterprise identifier. The method may also include sending the license key to an entity that provides configuration files for the mobile device application.

In some implementations, the enterprise may include a hospital. The enterprise identifier may include a hospital identifier.

BRIEF DESCRIPTION OF THE DRAWINGS

FIG. 5 shows examples of a data structure of a license key in accordance with some embodiments.

FIG. 6C depicts an exemplary database for recording pre-paid licenses that may have been purchased by an individual, organization, company or other group of users.

DETAILED DESCRIPTION

Figure 1:
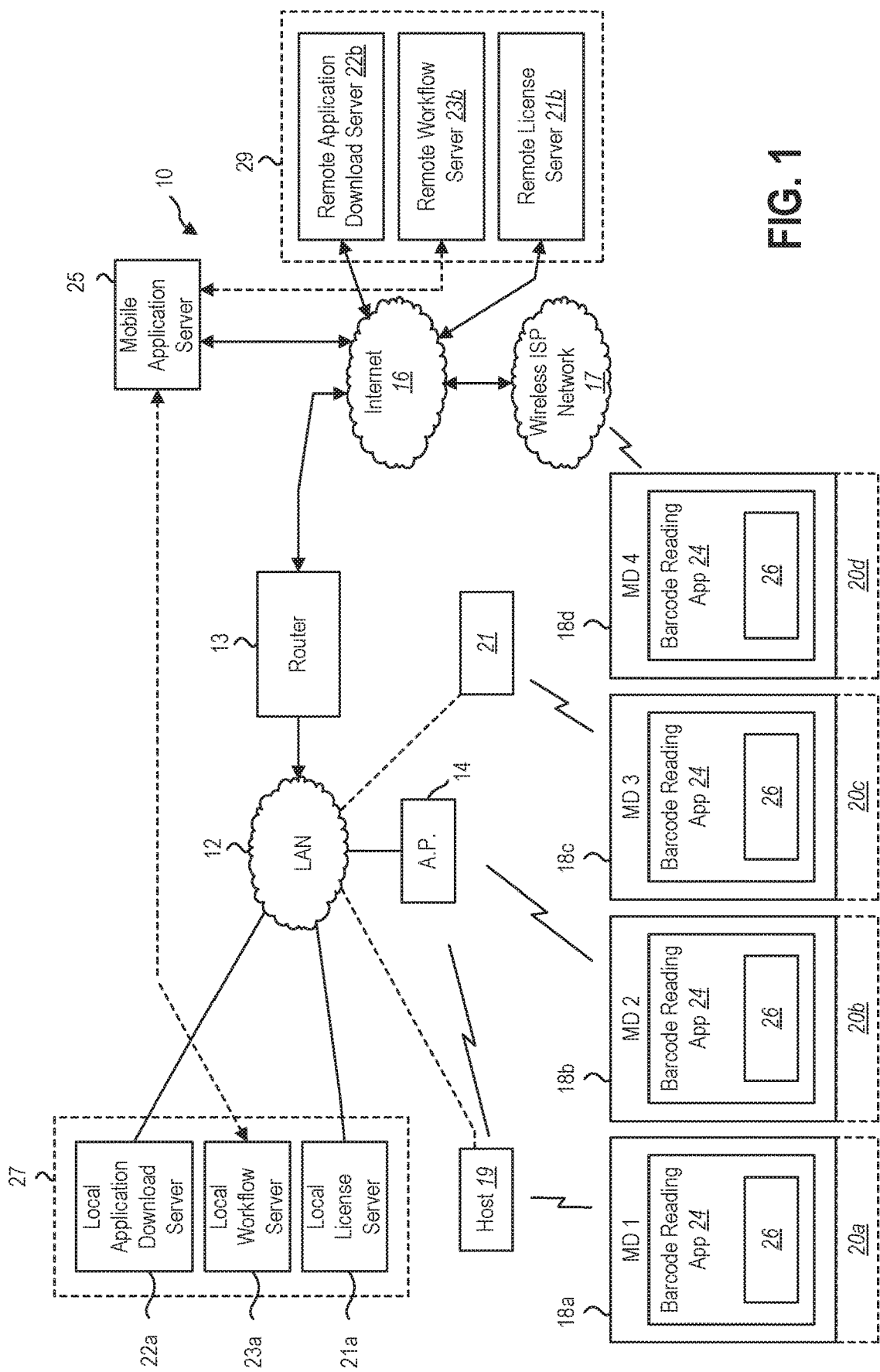
FIG. 1 illustrates an example of a barcode-reading system.

FIG. 1 depicts a system 10 according to one embodiment of the present application wherein mobile devices 18a-18d obtain: i) at least one barcode-reading application 24 from an application download server 22a or 22b; and ii) obtain licensing entitlements (e.g., a license key 26) necessary for the operation of the at least one barcode-reading application 24 on the mobile devices 18a-18d from a licensing server 21a or 21b and/or from an accessory 20a-20d secured to the mobile device 18a-18d.

As used in this patent specification and the accompanying claims, the term "mobile device" will be used to describe a portable, hand-held computing device that comprises a camera. As indicated above, one example of a mobile device is a smartphone. Another example of a mobile device is a tablet computer. Yet another example is a hybrid tablet/smartphone device, often nicknamed a "phablet."

The application download server may be, for example, a local application download server 22a or a remote application download server 22b. Similarly, the license server may be a local license server 21a or a remote license server 21b. The application download server and the license server may operate on distinct hardware or may operate on the same hardware server. For example, the local application download server 22a and the local license server 21a may operate on the same hardware server 27 or on distinct hardware servers, each coupled to a local area network (LAN) 12. Similarly, the remote application download server 22b and the remote license server 21b may operate on the same hardware server 29 or on distinct hardware servers, each coupled to the Internet 16.

The system 10 may include a LAN 12 to which each of the local application download server 22a and the local license server 21a are connected. The LAN 12 may further include at least one wireless access point 14 enabling LAN communications with mobile devices (for example, mobile devices 18b and 18c) as well as other computing systems such as a host computer 19 and/or a charging station 21 (e.g. a station for providing power to the mobile device 18 for charging its battery).

The LAN 12 may be coupled to the Internet 16 via a router 13.

Although FIG. 1 depicts the LAN 12 coupled to the Internet 16 via a single router 13, such connections may employ multiple routers and firewall systems, including demilitarized zone (DMZ) networks.

Figure 2:
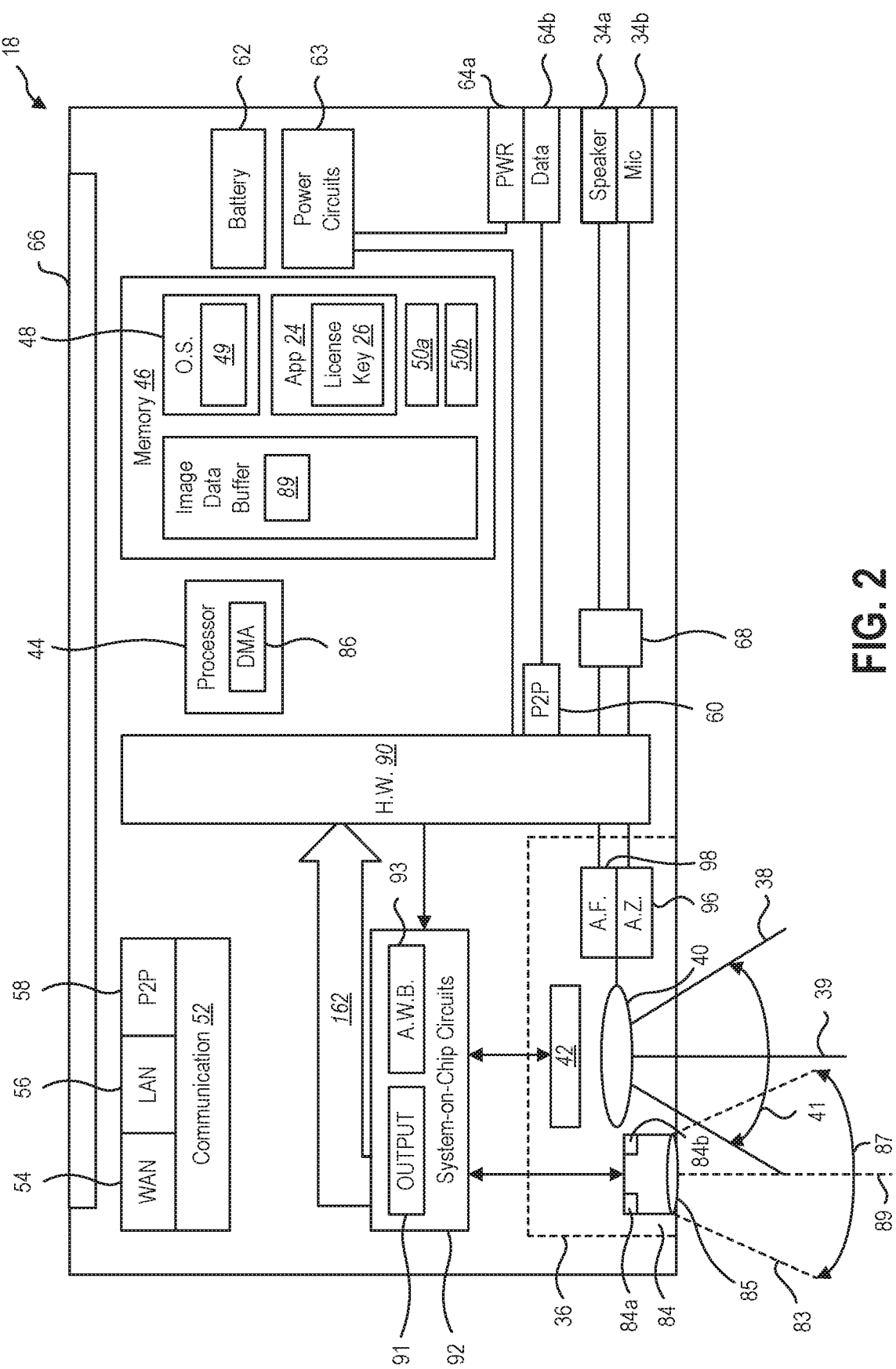
FIG. 2 is a block diagram of an exemplary mobile device useful in a barcode-reading system.

Referring to FIG. 2 in conjunction with FIG. 1, each of the mobile devices 18a-18d may include a wireless communication system 52 for operating within a wireless network environment. The wireless communication system 52 may comprise any permutation of: i) a local area network (LAN) communications module 56, ii) a wide area network (WAN) communications module 54, and/or iii) a wireless point-to-point communication interface 58.

The LAN communications module 56 may utilize Wi-Fi™ (IEEE 802.11) or similar wireless local area communication protocols for communication with a wireless access point 14 of a wireless portion of a LAN 12, such that the mobile device itself may be an addressable endpoint on the LAN 12, i.e., the mobile device may be assigned an IP address and may be capable of IP communications with other devices over the LAN 12 using IP protocols such as Transmission Connection Protocol (TCP), Uniform Datagram Protocol (UDP), etc. The wireless access point 14 and the LAN communications module 56 may function in accordance with any known wireless communications protocol, including but not limited to the IEEE 802.11 standards, which are sometimes referred to as Wi-Fi™. As will be discussed in more detail, a mobile device, 18b for example, utilizing its LAN communications module 56 may obtain at least one barcode-reading application 24 from an application download server 22a or 22b and its license key from a license server 21a or 21b via the LAN 12 and, as applicable, the Internet 16.

The WAN communications module 54 may utilize Wideband Code Division Multiple Access (WCDMA), High Speed Packet Access (HSPA), cdma2000, Long Term Evolution (LTE) technology, or other similar long-range wireless communication protocols for communication with a wide area wireless Internet service provider (ISP). For example, the ISP may be a mobile telephone service provider and the wireless WAN communications module 54 may be a system for wireless data communications with the access towers of the wireless ISP network 17 (i.e., WAN). Such wireless data communications may occur in accordance with any suitable wireless communication standard, including Third Generation (3G) standards (e.g., Universal Mobile Telecommunication Systems (UMTS), cdma2000, Enhanced Data Rate for GSM Evolution (EDGE), etc.) and/or Fourth Generation (4G) standards (e.g., LTE, Mobile WiMAX, etc.). The wireless ISP network 17 may assign an IP address to the mobile device such that the mobile device may be capable of IP communications with other devices over the wireless ISP network 17 using IP protocols such as TCP, UDP, or the like.

Remote devices (e.g., devices coupled to the Internet 16) may be logically connected to the LAN 12 using a Virtual Private Network (VPN) technology. As such, a mobile device, 18d for example, coupled to communicate with the wireless ISP network 17 utilizing its WAN communications module 54 may, utilizing a VPN technology, be an endpoint on the LAN 12. As such, a mobile device 18 may obtain at least one barcode-reading application 24 from the remote application download server 22b (or local application download server 22a utilizing VPN technologies) and its license key 26 from the remote license server 21b (or the local license server 21a utilizing VPN technologies) via the wireless ISP network 17 and, as applicable, the Internet 16.

The wireless point-to-point communication interface 58 may form a wireless point-to-point communication link with another compatible system, such as a host computer 19 and/or charging station 21, utilizing Bluetooth® or similar wireless point-to-point communication protocols. The host computer 19 and/or charging station 21 in turn includes a wired and/or wireless LAN interface for communication with a switch (not shown) or the wireless access point 14 of the LAN 12 such that the host computer 19 may be an addressable endpoint on the LAN 12. As will be discussed in more detail, a mobile device, 18a or 18c for example, coupled to communicate with the host computer 19 utilizing its wireless point-to-point communication interface 58 may obtain at least one barcode-reading application 24 from an application download server 22a or 22b and its license key 26 from a license server 21a or 21b via its point-to-point connection to the host computer 19 and/or charging station 21 which communicates with the servers via the LAN 12 and, as applicable the Internet 16.

The system 10 also includes workflow servers 23a-b, including a local workflow server 23a and a remote workflow server 23b, as well as a mobile application server 25. After the barcode-reading application 24 has been downloaded and installed on a mobile device 18, the barcode-reading application 24 may interact with one or more of the workflow servers 23a-b via the mobile application server 25.

Referring to FIG. 2, the mobile device 18 may include a processor 44 and memory 46 in electronic communication with the processor 44. The processor 44 may be embodied as a combination of one or more microprocessors, microcontrollers, digital signal processors (DSP), or the like, and, when operating, may execute instructions (in the form of an operating system and/or applications) stored in the memory 46. The memory 46 may be any component capable of storing electronic information, including an operating system and/or application instructions executable by the processor 44, and may be embodied as read-only memory (ROM), random access memory (RAM), magnetic disk storage media, optical storage media, flash memory devices, on-board memory included with the processor 44, erasable programmable read-only memory (EPROM), electrically erasable programmable read-only memory (EEPROM), and/or registers, etc.

The memory 46 may include an operating system 48, the barcode-reading application 24, the license key 26, one or more other applications 50a, 50b, and a data buffer including an image data buffer 89. In operation, the processor 44 may execute instructions embodied in the operating system 48, the barcode-reading application 24, and each of the other applications 50a, 50b. Hardware circuits 90 interface the processor 44 with peripheral systems including, but not limited to, a (multi-touch) display screen 66, a wireless communication system 52, a hardwired point-to-point communication interface 60, an audio interface 68, a camera assembly 36, and a white light source 84 (e.g., an illuminator or a flash for utilizing the camera assembly 36 for photography).

The hardwired point-to-point communication interface 60 may utilize Universal Asynchronous Receiver/Transmitter (UART), Universal Serial Bus (USB), and similar communication protocols for communicating with a compatible system connected to a data connector 64b (which may be a part of a single power/data connector such as a USB connector or an Apple® Lightning Connector®).

The audio interface 68 may include circuits for generating analog audio signals on a speaker connector 34a and receiving analog microphone input on a microphone connector 34b. The speaker connector 34a and the microphone connector 34b may be embodied as a single tip/ring/ring/sleeve (TRRS) connector typically referred to as a head-set connector.

Referring to FIG. 2, the camera assembly 36 may include a (color) photo sensor 42 (i.e., an array of image sensors). The photo sensor 42 may be positioned parallel to each of the face surface and the back surface of the mobile device 18. The camera assembly 36 may also include a lens assembly 40 with an optical axis 39 orthogonal to the photo sensor 42 and defining a center line of a camera field of view 38 extending outward from the back surface of the mobile device 18. The photo sensor 42 may include one or more sensors such as charge-coupled display (CCD) sensors, complementary metal-oxide-semiconductor (CMOS) sensors, or the like.

The lens assembly 40 may receive light reflected from objects within the camera field of view 38. The camera field of view 38 may have an angular size 41 which may be the angle at which the camera field of view 38 spreads with respect to distance from the lens assembly 40. The lens assembly 40 may have a camera aperture size measured as an f-number which is the ratio of the focal length of the lens assembly 40 to the diameter of the entrance pupil (i.e., the lens aperture (an aperture stop or an inherent aperture of the lens component defining the aperture) as viewed through the front of the lens assembly 40).

The camera assembly 36 may further include an auto zoom module 96 and/or an autofocus module 98 which may serve to control an optical zoom setting and/or autofocus setting of the camera, respectively. Autofocus and auto zoom may be controlled by moving the position of at least one of the lenses making up the lens assembly 40 with respect to each other (or with respect to the photo sensor 42) and/or altering the curvature of at least one of the lenses making up the lens assembly 40.

In general, the camera lens assembly 40 and the autofocus module 98 (which compensates for limited depth of field at larger apertures) and the auto zoom module 96 (which adjusts the angular size 41 and image magnification) are designed and/or optimized for general-purpose photography, and may therefore not be ideal for barcode capture and/or decoding. More specifically, in a barcode-reading application an operator expects to read and decode a barcode in less than 300 ms. The focus and zoom adjustment process may require significantly more time and therefore, if used, it would significantly delay the response time in a barcode-reading application.

If the camera lens assembly 40 is fixed (e.g., not adjusted for focus and zoom) at any particular focus and/or zoom setting for the lens assembly 40, the combination of the angular size 41 and the camera aperture size affect the camera depth of field (e.g., the range of distances at which a barcode of a particular modular size is imaged onto the photo sensor with sufficient size and sharpness for decoding). The angular size 41 affects the minimum distance at which a barcode of a certain overall size can be imaged onto the photo sensor 42.

The photo sensor 42 may be coupled to system-on-chip circuits 92 which include an output module 91 and an auto-white balance module 93. In one embodiment, the output module 91 may control the operation of the photo sensor 42 (e.g., exposure, gain, and coupling of pixels to analog-to-digital (A/D) converters for image read out), format the digital intensity values of each pixel of the photo sensor 42 for color image output, and make the color image output available for writing to the image data buffer 89.

In another embodiment, the output module 91 may perform image processing on images captured by the photo sensor 42. Control of the photo sensor 42 and image pre-processing which may be performed by the system on chip circuits 92 are described in more detail in U.S. patent application Ser. No. 14/717,112, entitled "BARCODE READER" and filed on May 20, 2015, which is hereby incorporated by reference in its entirety.

The auto-white balance module 93 may perform auto-white balance algorithms on the captured image to enhance the quality of color photographs captured by the photo sensor 42 under different illumination conditions. The digital image output 162 (which may be the color image or a result of processing the image one or more times in accordance with the teachings of U.S. patent application Ser. No. 14/717,112) may be written to the image data buffer 89. The mobile device 18 may include a direct memory access (DMA) system 86 which may be a part of the processor 44. The DMA system 86 provides for direct writing of the digital image output 162 from the camera assembly 36 to the image data buffer 89.

The camera assembly 36 may further include a white light source 84. The white light source 84 may include one or more LEDs 84*a*, 84*b* controlled by the system-on-chip circuits 92.

In an exemplary embodiment, a first LED 84*a* may be a white LED. The color of a white LED is typically described using a Kelvin temperature scale with 1500° K representing a warm color "white," such as that of candlelight, and 9500° K representing a cool color "white," such as that of a blue sky. The exemplary white LED may be within this range. Alternatively, the exemplary white LED may have a color between 4000° K and 7000° K.

In the exemplary embodiment the second LED 84*b* may be an amber LED emitting illumination within the 600-615 nm range. Both the first LED 84*a* and the second LED 84*b* may be positioned behind a common optic 85 which directs illumination within a field of illumination 83 projecting away from the back surface and having an illumination axis perpendicular to the back surface and an illumination angle 87 which substantially coincides with the field of view 38 of the camera assembly 36. In operation, the system-on-chip circuits 92 may control each LED 84*a*, 84*b* independently; and control the intensity of each LED 84*a*, 84*b* independently such that the color of the white illumination of the combined LEDs may be controlled by controlling the intensity of the amber LED with respect to the intensity of the white LED. If the intensity of the amber LED is higher, the white color of the combination will be warmer (lower Kelvin temperature). If the intensity of the amber LED is lower, the color approaches the Kelvin temperature of the white LED alone.

Returning to FIG. 2, the mobile device 18 may further include a battery 62 and power circuits 63. In general the power circuits 63 control charging of the battery 62 from power received from an external power source via the power connector 64*a* and providing operating power at the voltage and current drawing requirements of the various components of the mobile device 18 from the power received from the battery 62 or the external power source (when connected to the external power source).

Referring to FIG. 2 in conjunction with FIG. 1, in an exemplary embodiment, the operating system 48 may include an application retrieval system 49 which obtains the barcode-reading application 24 and the applications 50*a*, 50*b* from the application download server 22*a* or 22*b*. In one embodiment, the operation of the application retrieval system 49, which may obtain the barcode-reading application 24 and the other applications 50*a*, 50*b* from the application download server 22*a* or 22*b*, may be the exclusive means for loading, writing, or otherwise placing the barcode-reading application 24 and the other applications 50*a*, 50*b* into the memory 46. The operating system 48 may be configured to block or prevent loading of any applications to the memory 46 by any means other than the operation of the application retrieval system 49 in a manner such that the applications 24, 50*a*, 50*b* may be retrieved exclusively from the application download server 22*a* or 22*b*.

Figure 3A:
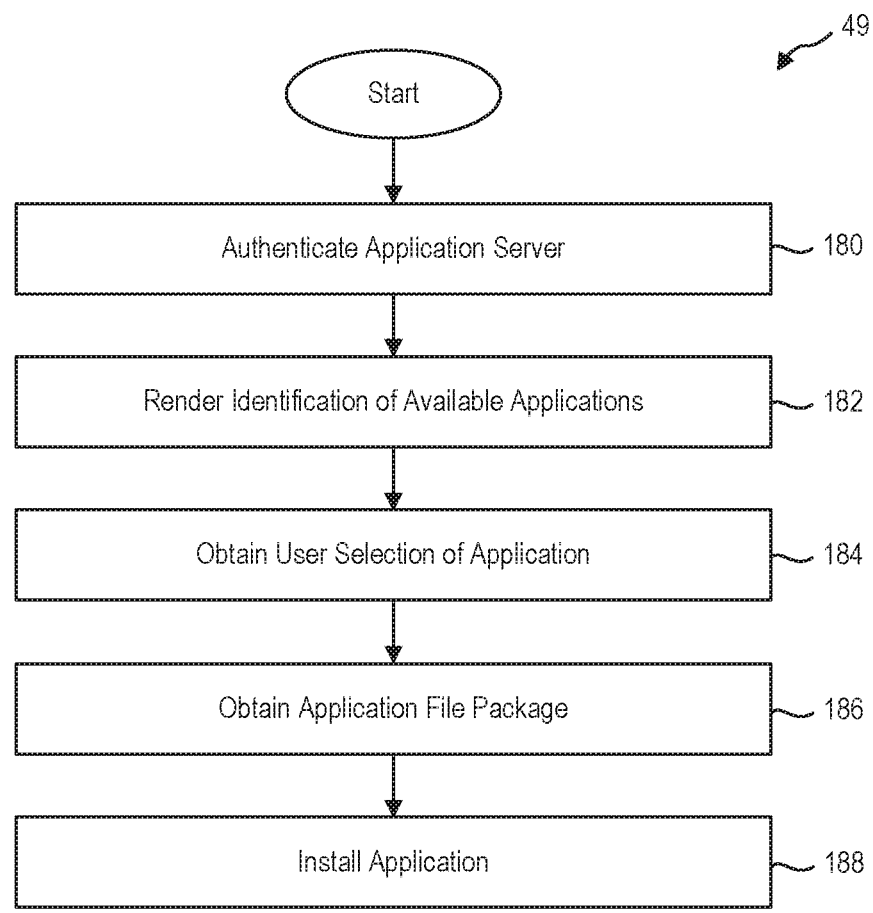
FIG. 3A is a flow diagram of an exemplary process for an operation of an application retrieval system.

FIG. 3A is a flow diagram of an exemplary process for the operation of the application retrieval system 49. Step 180 represents the application retrieval system 49 of the mobile device 18 establishing a secure connection to the application download server 22*a* or 22*b* over the LAN 12, the wireless ISP network 17 and/or the Internet 16 and authenticating the application download server 22*a*, 22*b* (i.e., mutual authentication between the mobile device and the application download server). The mutual authentication may be established by using any conventional authentication protocol.

Step 182 represents rendering, on the display screen 66 of the mobile device 18, identification of applications which are available to the mobile device 18 for downloading. Step 184 represents obtaining user selection of an application to download.

Step 186 represents obtaining an application file package (e.g., an install package) from the application download server 22*a* or 22*b*. The application file package may be temporarily stored in the memory 46 of the mobile device 18.

Step 188 represents installing the application. The installation process may include un-packing the install package and writing an executable application to the memory 46.

Figure 3B:
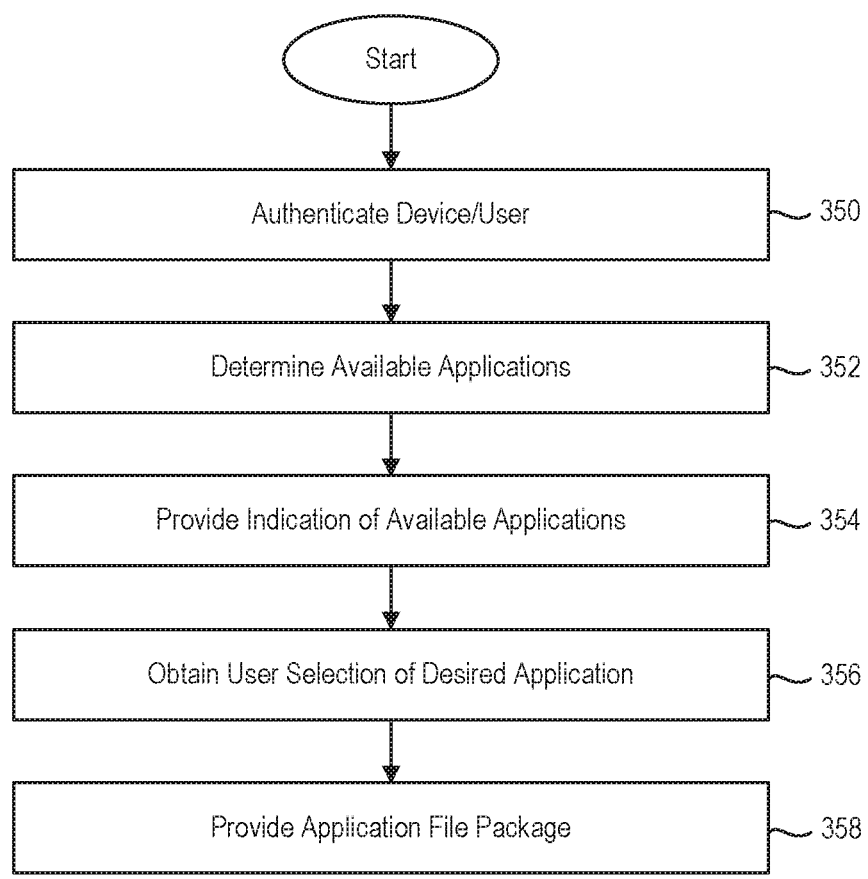
FIG. 3B is a flow diagram depicting an exemplary process for an operation of an application download server.

FIG. 3B is a flow diagram depicting an exemplary process for operation of an application download server 22*a*, 22*b*. Step 350 represents the application download server 22*a*, 22*b* establishing a secure connection with the mobile device 18 over the LAN 12, the wireless ISP network 17, and/or the Internet 16 and authenticating the mobile device 18 and/or the user of the mobile device 18. Authenticating the user of the mobile device 18 may include: i) authenticating the individual to which the mobile device 18 is assigned or the individual using the mobile device 18, utilizing a combination of a user ID and a password or similar schemes for authenticating an individual, and/or ii) authenticating an organization, company, or other group of users to which the mobile device 18 is assigned, utilizing a combination of a user ID and a password or other similar schemes for identifying whether the mobile device 18 has been assigned to the organization, company, or group and authenticating the assignment. The user ID may be unique to each mobile device 18 or common for all mobile devices 18 assigned to the organization, company, or group.

Step 352 represents the application download server 22*a*, 22*b* determining a plurality of one or more applications (the barcode-reading application 24, applications 50*a*, 50*b*, etc.) available for download based on the individual, organization, company, or other group to which the mobile device 18 is assigned.

Figure 3C:
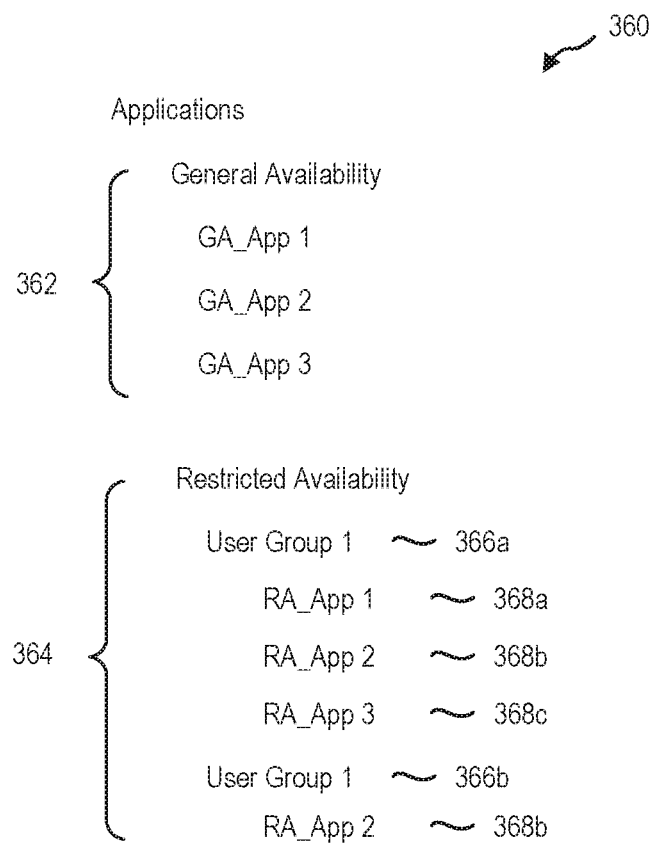
FIG. 3C shows an exemplary structure of a database of applications for downloading.

Turning briefly to FIG. 3C, the application download server 22a, 22b may contain, or have access to, a database 360 which identifies generally available applications 362 which are available to any mobile device 18 without regard to the identification of the user, organization, company, or group to which the mobile device 18 is assigned; and restricted applications 364 which are available only to certain individuals, organizations, companies, and groups. For restricted applications 364, the database 360 may associate each user group 366a, 366b with identification of those restricted applications available to that user group 366a, 366b. Each user group may be an individual, organization, company, or other group. For example, user group 1 366a may have access to restricted applications 368a, 368b, and 368c, and user group 2 366b may have access to restricted application 368b. In each case these restricted applications may be applications written custom for the user group (and therefore are not made available to other user groups) or may be licensed to the user group (and therefore made available to those user groups which obtained a license for the application).

Returning to FIG. 3B, step 354 represents the application download server 22a, 22b providing an indication of the available applications to the mobile device 18. The available applications may include any of the generally available applications 362 and/or the restricted applications 364. The indication of the available applications may include, for each application, a display screen icon representing the application. The indication of available applications may not include all available applications but may include only those available applications within parameters established by the user, for example available applications which meet search criteria provided by the user. As such, step 354 may include making a search function available to the mobile device 18, obtaining search criteria or search terms from the user of the mobile device 18, and selecting matching applications that meet the search criteria from the applications available to the individual, organization, company, or group.

Step 356 represents the application download server 22a, 22b obtaining a user selection of a desired application. The desired application may be one of the available applications indicated to the user at step 354.

Step 358 represents the application download server 22a, 22b providing an application file package for the desired application to the mobile device 18. The application file package may be provided to the application retrieval system 49 of the mobile device 18 which is provided for writing the file package to a non-volatile memory and unpacking and loading the contents of the file package to generate instructions which, when loaded to a memory, may be executed by the processor 44.

Certain applications such as the barcode-reading application 24 may: i) require a license key from a license server 21a, 21b to enable operation of the application, ii) operate in a base mode of operation without a license key but require a license key from a license server 21a, 21b to enable at least one enhanced function to operate in an enhanced mode of operation, and/or iii) require a license key from a license server 21a, 21b to continue operating, or continue operating in the enhanced mode of operation, following the passage of time or following a threshold level of usage based on the time and/or the quantity of instances with which certain functions were performed (such as the quantity of decoding a barcode of a certain symbology or symbologies).

The at least one enhanced function may be a function of decoding a barcode symbology that the barcode-reading application 24 (e.g., the decoder) is restricted from decoding in the base mode of operation. Alternatively or additionally, the at least one enhanced function may be a function of decoding multiple barcodes in sequence at a rate that is faster than a rate at which the barcode-reading application 24 (e.g., the decoder) can decode multiple barcodes in sequence in the base mode of operation. Alternatively or additionally, the at least one enhanced function may be a function of decoding a quantity of barcodes of a particular symbology that exceeds a restricted threshold quantity of barcodes of the particular symbology that the barcode-reading application 24 (e.g., the decoder) can decode in the base mode of operation.

Alternatively or additionally, the at least one enhanced function may remove a demonstration restriction function (i.e., a demonstration factor that makes output of decoded data useful for demonstration purposes only) under which the barcode-reading application 24 functions in the base mode of operation. The demonstration restriction function may be at least one of: i) a function that scrambles decoded data from a barcode of at least one symbology, ii) a function that restricts the decoded data or scrambled decoded data from a barcode of at least one symbology from being made available for further processing, or iii) a function that restricts the decoded data or the scrambled decoded data from a barcode of at least one symbology from being displayed on a display screen of the mobile device 18.

Alternatively or additionally, the at least one enhanced function may enable at least one enhanced image processing function that improves an ability to decode an image of a barcode and is not operable when the decoder operates in the base mode of operation. The enhanced image processing function may include preforming additional image processing algorithms which alter the image captured by the camera assembly 36 prior to execution of the algorithms which attempt to decode a barcode depicted within the image.

In accordance with another embodiment, the base mode of operation may include a base decoding mode of operation and a demonstration mode of operation. In the base decoding mode of operation, the barcode-reading application 24 may drive the camera assembly 36 to capture an image of a barcode and apply base decoder functions to the image to identify a barcode symbology. The barcode-reading application 24 may decode the barcode and make decoded data available for further processing if the barcode symbology is a base symbology, and enter the demonstration mode of operation if the barcode symbology is not the base symbology.

In the demonstration mode of operation, the barcode-reading application 24 may apply at least one enhanced barcode-reading function to decode the barcode, and perform at least one of: i) outputting an indication of successful decoding of the barcode, or ii) implementing a restriction function. The restriction function may be at least one of: i) a function that scrambles decoded data, ii) a function that restricts the decoded data or scrambled decoded data from being made available for further processing by at least one application executing on the mobile device, or iii) a function that restricts the decoded data or the scrambled decoded data from being displayed on a display screen of the mobile device 18.

The barcode-reading application 24 may perform an upgrade function in the demonstration mode of operation. The upgrade function may enable user selection to obtain the license code, obtain the license code based on the user selection, establish a network connection to the licensing server 21a, 21b, and obtain the license code from the licensing server 21a, 21b.

In order to obtain the license code from the licensing server 21a, 21b, the barcode-reading application 24 may communicate to the licensing server 21a, 21b one of: i) a unique identification code of the mobile device 18, or ii) a user identification code identifying a controller of the mobile device 18.

In accordance with another embodiment, the barcode-reading application 24 (e.g., a decoder application) running on the processor 44 of the mobile device 18 may be configured to control the camera assembly 36 of the mobile device 18 to capture an image of a barcode. The image of the barcode may be affected by at least one optic system of the camera assembly 36. The decoder application may utilize a base decoder function for attempting to decode a barcode if an enhanced decoder mode has not been authorized for the mobile device 18, and utilize an enhanced decoder function for attempting to decode the barcode if the enhanced decoder mode has been authorized for the mobile device 18.

The enhanced decoder function may include a function of decoding a barcode symbology that the decoder application is restricted from decoding if the enhanced decoder mode has not been authorized for the mobile device 18. Alternatively or additionally, the enhanced decoder function may include a function of decoding multiple barcodes in sequence at a rate that is faster than a restricted rate at which the decoder application can decode a sequence of multiple barcodes if the enhanced decoder mode has not been authorized for the mobile device 18. Alternatively or additionally, the enhanced decoder function may include a function of decoding a quantity of barcodes of a particular symbology that exceeds a restricted quantity of barcodes of the particular symbology which the decoder application can decode if the enhanced decoder mode has not been authorized for the mobile device 18. Alternatively or additionally, the enhanced decoder function may remove a demonstration restriction function (i.e., a demonstration factor that makes output of decoded data useful for demonstration purposes) under which the decoder application functions when the enhanced decoder mode has not been authorized for the mobile device 18, thereby making decoded data from a barcode of a particular symbology available for further processing by an application executing on the mobile device 18. The demonstration restriction function may be at least one of: i) a function which scrambles decoded data from a barcode of at least one particular symbology, ii) a function which restricts the decoded data or scrambled decoded data from a barcode of at least one particular symbology from being made available for further processing by at least one application executing on the mobile device 18, or iii) a function which restricts the decoded data or the scrambled decoded data from a barcode of at least one particular symbology from being displayed on a display screen of the mobile device 18. Alternatively or additionally, the enhanced decoder function may enable at least one enhanced image processing function which improves an ability to decode an image of a barcode and is not operable if the enhanced decoder mode has not been authorized for the mobile device 18. The enhanced decoder mode may be authorized by obtaining a license code from a licensing server 21a, 21b.

The decoder application may be configured to subject the license code to a predetermined algorithm to determine at least one operating permission authorized by the license code. The enhanced decoder function may correspond to the at least one operating permission authorized by the license code. The decoder application or any other application may be further configured to obtain the license code from the licensing server 21a, 21b by communicating to the licensing server one of: i) a unique identification code of the mobile device 18, or ii) a user identification code identifying a controller of the mobile device 18.

The barcode-reading application 24 (and the decoder application) disclosed above may be embodied on a computer-readable medium. The barcode-reading application 24 (and the decoder application) includes instructions executable by the processor 44 of the mobile device 18 for performing the functions disclosed above.

Figure 4A:
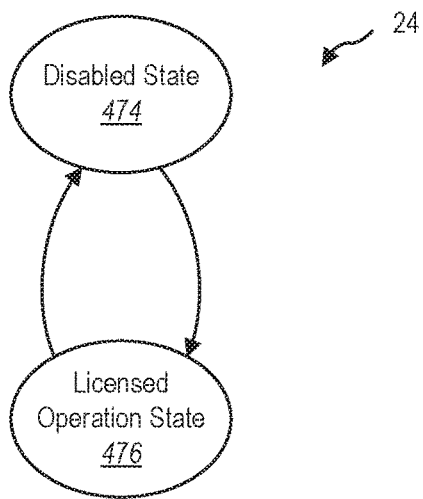
FIG. 4A is a state machine diagram depicting two states of operation in a barcode-reading application in accordance with one embodiment.

FIG. 4A is a state machine diagram depicting two states of operation in a barcode-reading application 24 in accordance with one embodiment. The first state of operation may be a disabled state 474 (which may also be referred to as a base state). In the disabled state 474, at least one function of the barcode-reading application 24 is disabled such that the barcode-reading application 24 may not output useful decoded data for further processing or transmission by the barcode-reading application 24 but may be capable of connecting to a licensing server 21a, 21b to obtain a license to transition the barcode-reading application 24 to a licensed operation state 476 (which may also be referred to as an enhanced operation state). The at least one function that may be disabled includes: i) an image capture function which, if enabled, would enable capturing an image of a barcode for image processing and decoding, ii) a decoding function which, if an image of a barcode is captured, would decode the image of the barcode to generate decoded data, iii) a data processing function which, if decoded data is generated, would process the decoded data as part of a useful workflow, and/or iv) a data transmission function which, if decoded data is generated and/or processed by the barcode-reading application 24, would make the decoded data available to another local application (e.g., another application on the mobile device 18) or a remote application (e.g., another application or database on any of the host computer 19, a local server coupled to the LAN 12, or a remote server coupled to the Internet 16.

The licensed operation state 476 may enable the function(s) that is/are disabled when the barcode-reading application 24 is in the disabled state 474 such that the barcode-reading application 24 may be capable of capturing an image of a barcode for image processing and decoding, decoding the image of the barcode to generate decoded data, and performing, as applicable: i) a data processing function which, if decoded data is generated, would process the decoded data as part of a useful workflow, and ii) a data transmission function which, if decoded data is generated and/or processed by the barcode-reading application 24, would make the decoded data available to another local application (e.g., another application on the mobile device 18) or a remote application (e.g., another application or database on any of the host computer 19, a local server coupled to the LAN 12, or a remote server coupled to the Internet 16.

There may be two sub-embodiments of the licensed operation state 476. In a first sub-embodiment, all of the functions of the barcode-reading application 24 may be enabled. In a second sub-embodiment, all functions of the barcode-reading application 24 may be enabled except restrictions on the output of useful decoded data may be implemented. The restrictions may be specified in the license key which transitions the barcode-reading application 24 from the disabled state 474 to the licensed operation state 476. The restrictions may be symbology restrictions, time restrictions, and/or quantity restrictions.

FIG. 5 shows examples of a data structure of a license key in accordance with some embodiments. A first example license key 502 may include data fields (that may be encrypted) which specify the symbologies 508 (for example, symbologies A, B, and C that correspond to a Universal Product Code (UPC), a Quick Response (QR) Code, and a Portable Data File (PDF-417) and a lease term 510. The lease term 510 may specify a date and time at which the license key 502 expires. In response to receipt of this license key 502 (and decryption of the license key 502 if encrypted) the barcode-reading application 24 may transition to the licensed operation state 476, decode the specified symbologies 508 when in the licensed operation state 476 (while remaining disabled for decoding other symbologies not specified in the license, for example for a Data Matrix), and at the end of the lease term 510, transition back to the disabled state 474 (unless a new license key with an updated lease term 510 is received prior to expiration, which functions to extend the expiration of the lease term).

A second example license key 504 may include data fields (that may be encrypted) which specify the symbologies 512a-c (for example, symbologies A, B, and C that correspond to a UPC, a QR Code, and a PDF-417), and a licensed quantity of decodes 514a-c for each symbology 512a-c. The licensed quantity of decodes for a particular symbology, for example the licensed quantity 514a for symbology 512a, may be unlimited. The licensed quantity of decodes 514b-c for symbologies 512b-c may be limited to a specified quantity. The entire license key 504 may further include a lease term 515 which may specify a date and time at which the license key 504 expires. In response to receipt of this license key 504 (and decryption of the license key 504 if encrypted) the barcode-reading application 24 may transition to the licensed operation state 476, and decode the specified symbologies 512a-c when in the licensed operation state 476 up to the licensed quantities 514a-c. The barcode-reading application 24 may remain disabled for decoding other symbologies not specified in the license (e.g., symbologies other than 512a-c), automatically disable each of symbologies 512b-c when the total quantity of decodes of each symbology 512b-c exceeds the licensed quantity 514b-c (unless a new license key increases the quantity), and transition back to the disabled state 474 (unless a new license key with an updated lease term is received prior to expiration, which functions to extend the expiration of the lease term 515). In this arrangement, the ability to decode symbologies 512b-c will expire upon the earlier of: i) reaching the maximum quantity of decodes 514b-c, or ii) expiration of the lease term 515.

A third example license key 506 may include data fields (that may be encrypted) which specify the symbologies 518a-c (for example, symbologies A, B, and C that correspond to a UPC, a QR Code, and a PDF-417), a license term 520a-c for each symbology 518a-c, and a licensed quantity 522a-c for each symbology 518a-c. The license term 520a-c may specify a date and time at which the license for that particular symbology 518a-c expires. The license term may be perpetual (e.g., license term 520a-b) or time limited (e.g., license term 520c). The licensed quantity of decodes for a particular symbology may be unlimited (e.g., the licensed quantity 520a for symbology A 518a), or may specify a specific quantity (e.g., the licensed quantity 520b-c for symbology B 518b and symbology C 518c).

In response to receipt of this license key 506 (and decryption of the license key 506 if encrypted) the barcode-reading application 24 may transition to the licensed operation state 476, and decode the specified symbologies 518a-c when in the licensed operation state 476 up to the licensed quantities 522a-c for each symbology and for the duration of the license term 520a-c for each symbology. The barcode-reading application 24 may remain disabled for decoding other symbologies not specified in the license (e.g., symbologies other than 518a-c), and automatically disable each of symbologies 518b-c when the earlier of: i) the expiration of the license term 520a-c for each symbology 518a-c expires, or ii) the total quantity of decodes of each symbology 518b-c exceeds the licensed quantity 522b-c, each being subject to extension by a new license key with an increased term duration or an increased quantity.

Each of the license keys 502, 504, 506 may be a data file, specifying the symbologies, the license terms, and the license quantities as depicted in FIG. 5. The data file may be encrypted utilizing an encryption key (e.g., a private key of a public/private key pair). The encrypted data file may form the license key and may be decrypted by the barcode-reading application 24 utilizing an encryption key (e.g., a public key of the public/private key pair). Other known encryption technologies may also be utilized for securing the delivery of the license key to the barcode-reading application 24 including the license restrictions (e.g., licensed symbologies, license terms, and licensed quantities) within the license key.

Each of the license keys 502, 504, 506 shown in FIG. 5 includes an enterprise identifier (ID) 516. The enterprise ID 516 may be a value that is required for access to the data that is associated with a particular enterprise. Additional information about the enterprise ID 516 and its possible uses will be provided below.

Figure 4B:
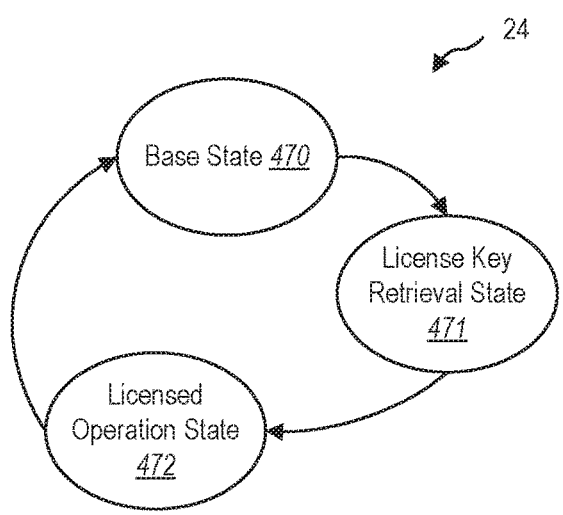
FIG. 4B is a state machine diagram depicting three states of operation in a barcode-reading application in accordance with another embodiment.

FIG. 4B is a state machine diagram depicting three states of operation in a barcode-reading application 24 in accordance with another embodiment. The first state of operation may be a base state 470. When in the base state, the barcode-reading application 24 may include barcode-reading capabilities which, although functional and capable of generating useful decoded data, are limited by at least one factor or function (which will be referred to as a demonstration factor) which makes output of decoded data useful for demonstration purposes but not practical for ongoing operation.

The operation of the barcode-reading application 24 in the base state may be a base decoding mode of operation or a demonstration mode of operation. In the base decoding mode of operation, the barcode-reading application 24 may drive the camera of the mobile device 18 to capture an image of a barcode, and apply base decoder functions to the image to identify the barcode symbology. If the barcode symbology is a base symbology, the barcode-reading application 24 may decode the barcode and make the decoded data available for further processing. If the symbology is other than a base symbology, the barcode-reading application 24 may enter the demonstration mode of operation.

In the demonstration mode of operation, the barcode-reading application 24 may apply at least one unlicensed enhanced barcode-reading function to decode the barcode, and perform at least one of: i) outputting an indication of successfully decoding the barcode, or ii) implementing a restriction function. The restriction function may be at least one of: i) a function which scrambles decoded data; ii) a function which restricts the decoded data or scrambled decoded data from the barcode from being made available for further processing by at least one application executing on the mobile device; or iii) a function which restricts the decoded data or the scrambled decoded data from the barcode from being displayed on a display screen of the mobile device.

The at least one demonstration factor may include, but is not limited to: i) a scrambling function which, upon generating decoded data, provides the output in a scrambled or truncated format for purposes of demonstrating decoding capabilities (and decoder performance) but preventing use of the decoded data for further data processing, ii) a time delay function which, upon generating and outputting decoded data (or scrambled decoded data), provides for implementing a time delay before a barcode of the same symbology can again be successfully decoded, iii) an output restriction function which restricts decoded data (or scrambled decoded data) from being made available for further processing by at least one application executing on the mobile device 18, and iv) an output restriction function which enables outputting decoded data (or scrambled decoded data) to the display screen and prevents the decoded data from being further processed by the mobile device 18 (other than presentation on the display screen) or transmission to a remote application.

The demonstration mode of operation may include an upgrade function. The upgrade function may enable user selection to obtain the license code and upon user selection to obtain the license code, establish the network connection to the licensing server and obtain the license code from the licensing server 21a, 21b.

The at least one demonstration factor may be applied to selected symbologies or all symbologies. Different demonstration factors may be applied to different symbologies.

The barcode-reading application 24 may transition from the base state 470 to a license key retrieval state 471. Reading a barcode to which a demonstration factor applies may trigger transition of the barcode-reading application 24 to the license key retrieval state 471. Alternatively, the barcode-reading application 24 may transition to the license key retrieval state 471 upon user selection of the license key retrieval state 471.

When in the license key retrieval state 471 the barcode-reading application 24 may connect to a licensing server 21a, 21b to obtain a license key. After obtaining the license key, the barcode-reading application 24 may transition to a licensed operation state 472 (i.e., an enhanced operation state).

The licensed operation state 472 may enable the barcode-reading application 24 to function without limitations of the at least one demonstration factor such that the barcode-reading application 24 may be capable of capturing an image of a barcode for image processing and decoding, decoding the image of the barcode to generate decoded data, and performing, as applicable: i) a data processing function which, if decoded data is generated, would process the decoded data as part of a useful workflow, and ii) a data transmission function which, if decoded data is generated and/or processed by the barcode-reading application 24, would make the decoded data available to another local application (e.g., another application on the mobile device 18) or a remote application (e.g., another application or database on any of the host computer 19, a local server coupled to the LAN 12, or a remote server coupled to the Internet 16), in each case without being impeded by the demonstration factor.

As described with respect to the licensed operation state 476 in FIG. 4A, there may be two sub-embodiments of the licensed operation state 472. In a first sub-embodiment, all of the functions of the barcode-reading application 24 may be enabled. In a second sub-embodiment, all functions of the barcode-reading application 24 may be enabled except restrictions on the output of useful decoded data may be implemented. The restrictions may be specified in the license key which transitions the barcode-reading application 24 to the licensed operation state 472. The restrictions may be symbology restrictions, time restrictions, and/or quantity restrictions.

Figure 6A:
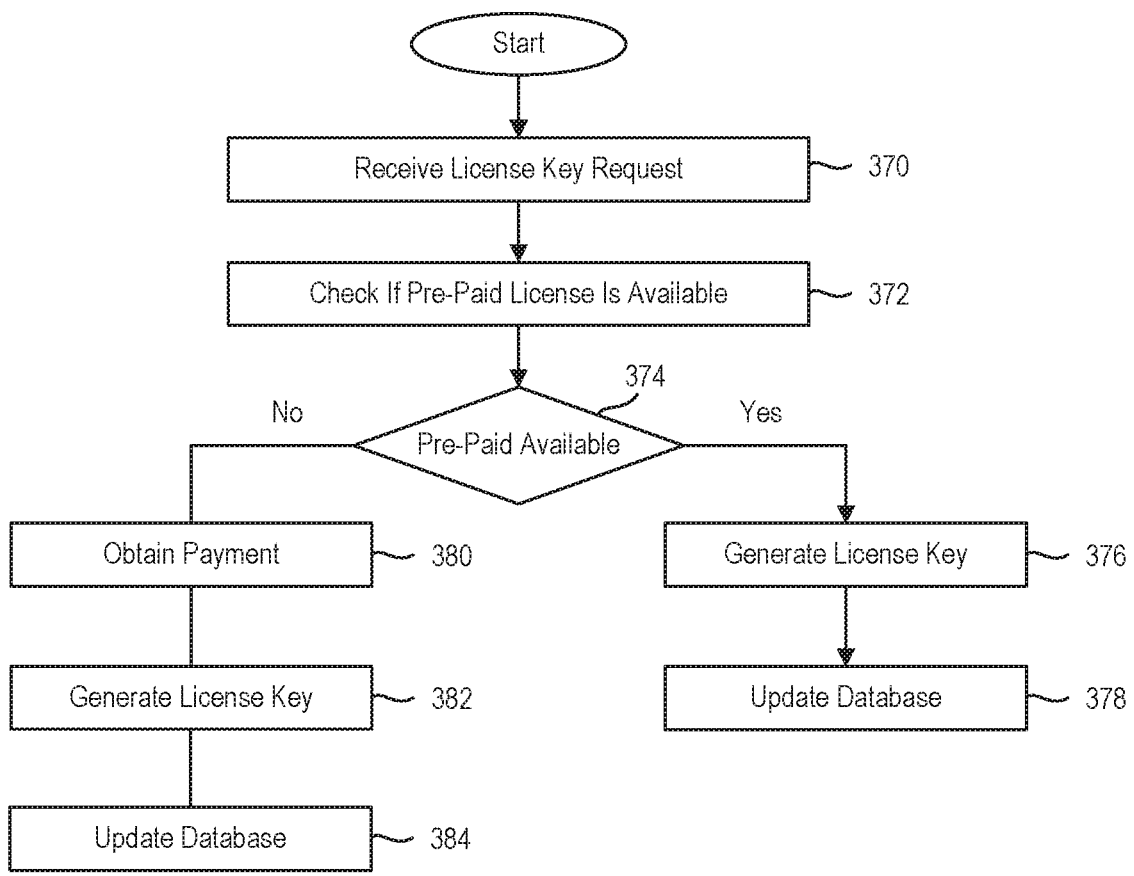
FIG. 6A depicts an exemplary operation of a license server.

FIG. 6A depicts an exemplary operation of a license server 21a, 21b. Step 370 represents receiving a license key request from the barcode-reading application 24 (or other application) of the mobile device 18. Receiving the license key request may include authenticating the user of the mobile device 18. Authenticating the user of the mobile device 18 may include: i) authenticating the individual to which the mobile device is assigned or the individual using the mobile device (or the individual who controls the mobile device), for example utilizing a combination of a user ID and a password or similar schemes for authenticating an individual, and/or ii) authenticating an organization, company, or other group of users to which the mobile device is assigned, for example utilizing a combination of a user ID and a password or other similar schemes for identifying whether the device has been assigned to the organization, company, or group and authenticating the assignment. The user ID may be unique to the device or common for all mobile devices 18 assigned to the organization, company, or group.

Step 372 represents the license server 21a, 21b checking whether a pre-paid license is available for the mobile device 18. More specifically, the identity of the individual, organization, company, or other group of users identified during the authentication may be used to look up (e.g., in a license database) licenses available to that individual, organization, company, or other group of users (if any). For a particular individual, organization, company, or other group of users, a certain quantity of licenses may have been pre-purchased.

FIG. 6C depicts an exemplary database 739 for recording pre-paid licenses that may have been purchased by an individual, organization, company or other group of users. Each such individual, organization, company or other group of users may be identified by a group ID 740, 750. Associated with each group ID is one or more license IDs 742, 752a, 752b, each of which identifies a license type for the barcode-reading application 24 which may have been purchased in quantities of one or more. Each license type may be, as an example, one of the license types identified by the license keys 502, 504, 506 of FIG. 5.

Each license ID 742, 752a, 752b may be associated with identification of: i) the quantity of the license type purchased 744, 754a, 754b, ii) the quantity used 746 or the quantity in use 756a, 756b, and/or iii) the quantity remaining 748, 758a, 758b for issuance to mobile devices 18. It should be appreciated that recording both the quantity used 746 or the quantity in use 756a, 756b as well as the quantity remaining 748, 758a, 758b for issuance to mobile devices is duplicative as either value can be calculated from the quantity purchased 744, 754a, 754b and the other value.

Recording the quantity used 746 is useful when licenses are purchased for a single mobile device, and once a license is issued to a particular mobile device it is permanently associated with that mobile device and may not be re-assigned to another mobile device without manual intervention.

Recording the quantity in use 756a, 756b is useful when the licenses are concurrent-use licenses, and when a license assigned to a mobile device expires it is considered no longer in-use and can be reassigned to another mobile device 18.

It should also be appreciated that if the quantity of licenses purchased is unlimited 754*a*, it is irrelevant to track in-use licenses 756*a*, 756*b* and remaining licenses 758*a*, 758*b*. When utilizing the concurrent-use licenses, for the in-use licenses 756*b*, the database may include an in-use table 760 which records, for each license 762, the time 764 at which it expires (e.g., the lease term 510 from FIG. 5) such that upon expiration (if the expiration is not updated by way of renewal), the license will revert to remaining inventory 758*b* and can be issued to a different mobile device 18.

It should be appreciated that this licensing scheme enables a mobile device 18 to obtain a license for a specific term, and so long as the mobile device 18 obtains a renewal license prior to expiration, the barcode-reading application 24 can operate under the license even if the mobile device is (periodically) uncoupled from any network and unable to contact the license server 21*a*, 21*b*.

Returning to FIG. 6A, step 374 represents determining whether a pre-paid license is available. If a prepaid license is available at step 374, a license key for the pre-paid license is generated at step 376 and the database 739 is updated at step 378. Updating the database may include recording the license as used 746 or in use 756*b*.

If it is determined at step 374 that a pre-paid license is not available, payment is obtained for a license at step 380. Step 380 may involve determining the type of license being requested (e.g., as identified by license keys 502, 504, 506), including the licensed symbology(ies) as well as license term(s) and license quantity(ies) for each symbology(ies). In one embodiment, the barcode-reading application 24 may, under the control of the license server 21*a*, 21*b*, generate a menu for user selection of these license parameters (i.e., symbologies, license terms and license quantities) and display on a screen of the mobile device 18 pricing alternatives for desired license parameters.

After payment is obtained, a license key for the license is generated at step 382 and the database 739 is updated at step 384 to reflect a newly purchased license for a user (group ID). If the newly purchased license is a concurrent-use license, updating the database may include recording the license as well as its expiration.

As stated, this licensing scheme enables a mobile device 18 to obtain a license for a specific term, and so long as the mobile device 18 obtains a renewal license prior to expiration, the barcode-reading application 24 can continue operation under the license even if the mobile device 18 is uncoupled from any network and unable to contact the license server 21*a*, 21*b*.

Figure 6B:
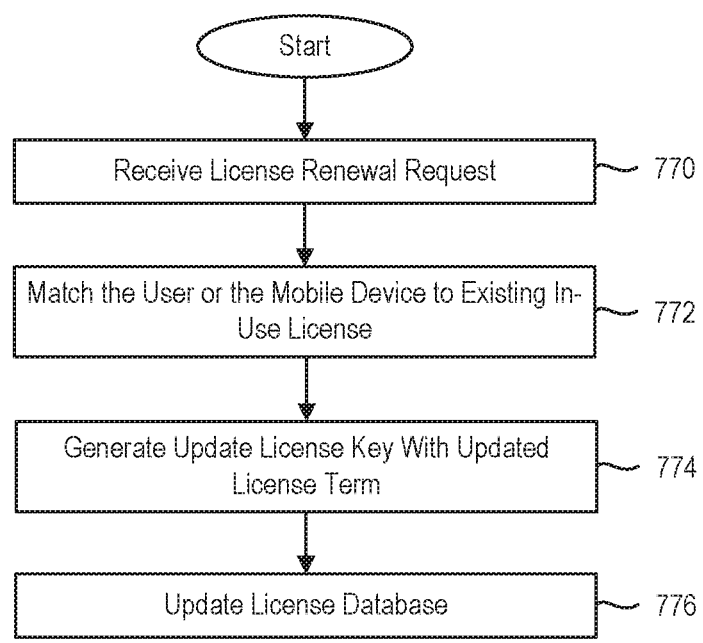
FIG. 6B depicts an exemplary operation of a license server for renewing a license for a mobile device prior to expiration of the license.

FIG. 6B depicts an exemplary operation of a license server 21*a*, 21*b* for renewing a license for a mobile device 18 prior to the expiration of the license (e.g., prior to the in-use license 756*b* reverting to a remaining license 758*b*).

Step 770 represents receiving a license key renewal request from the barcode-reading application 24 (or other application) of the mobile device 18. Receiving the license key renewal request may include authenticating the user of the mobile device 18. Authenticating the user of the mobile device 18, as discussed, may include: i) authenticating the individual to which the mobile device is assigned, or the individual using the mobile device (or the individual who controls the mobile device), for example utilizing a combination of a user ID and a password, or similar schemes for authenticating an individual, and/or ii) authenticating an organization, company, or other group of users to which the mobile device is assigned, for example utilizing a combination of a user ID and a password or other similar schemes for identifying whether the device has been assigned to the organization, company, or group and authenticating the assignment. The user ID may be unique to the device or common for all mobile devices 18 assigned to the individual, organization, company, or group. The mobile device 18 (e.g., the barcode-reading application) may communicate to the licensing server i) a unique identification code of the mobile device 18 or ii) a user identification code identifying a controller of the mobile device 18.

Step 772 represents the license server 21*a*, 21*b* matching the user or the mobile device 18 to the existing in-use license, which may be recorded in an in-use table (for example, the in-use table 760 shown in FIG. 6C).

Step 774 represents generating, and providing to the mobile device 18, an update license key which, as depicted by license key 502 of FIG. 5, may include an updated license term.

Step 776 represents updating the license database such that the expiration date of the license in the in-use table 760 is updated.

As disclosed above, the barcode-reading application 24 may be configured to operate in a base mode or an enhanced mode. In the base mode of operation, the barcode-reading application 24 may be configured to control a network interface of the mobile device 18 to establish a network connection to a licensing server 21*a*, 21*b* and obtain a license code from the licensing server 21*a*, 21*b*; subject the license code to a predetermined algorithm and determine at least one operating permission authorized by the license code; and enable an enhanced mode of operation. In the enhanced mode of operation, the barcode-reading application 24 may be configured to implement at least one enhanced barcode-reading function which corresponds to the at least one operating permission authorized by the license code.

The at least one enhanced barcode-reading function may include a function of decoding a barcode symbology that the decoder is restricted from decoding in the base mode of operation. Alternatively or additionally, the at least one enhanced barcode-reading function may include a function of decoding multiple barcodes in sequence at a rate that is faster than a rate at which the barcode-reading application can decode multiple barcodes in sequence in the base mode of operation. Alternatively or additionally, the at least one enhanced barcode-reading function may include a function of decoding a quantity of barcodes of a particular symbology that exceeds a restricted quantity of barcodes of the particular symbology that the barcode-reading application can decode in the base mode of operation.

Alternatively or additionally, the at least one enhanced barcode-reading function may remove a demonstration restriction function under which the barcode-reading application 24 functions in the base mode of operation. The demonstration restriction function may be at least one of: i) a function that scrambles decoded data from a barcode of at least one symbology, ii) a function that restricts the decoded data or scrambled decoded data from a barcode of at least one symbology from being made available for further processing, or iii) a function that restricts the decoded data or the scrambled decoded data from a barcode of at least one symbology from being displayed on a display screen of the mobile device 18.

Alternatively or additionally, the at least one enhanced barcode-reading function may enable at least one enhanced image processing function that improves an ability to decode an image of a barcode and is not operable when the decoder operates in the base mode of operation.

The base mode of operation may include a base decoding mode of operation and a demonstration mode of operation. In the base decoding mode of operation, the barcode-reading application may be configured to drive the camera assembly to capture an image of a barcode, and apply base decoder functions to the image to identify a barcode symbology. The barcode-reading application 24 may decode the barcode and make decoded data available for further processing if the barcode symbology is a base symbology, and enter the demonstration mode of operation if the barcode symbology is not the base symbology. In the demonstration mode of operation, the barcode-reading application 24 may be configured to: apply at least one enhanced barcode-reading function to decode the barcode, and perform at least one of outputting an indication of successful decoding of the barcode or implementing a restriction function. The restriction function may be at least one of: i) a function that scrambles decoded data, ii) a function that restricts the decoded data or scrambled decoded data from being made available for further processing by at least one application executing on the mobile device 18, or iii) a function that restricts the decoded data or the scrambled decoded data from being displayed on a display screen of the mobile device 18.

The barcode-reading application 24 may be configured to perform an upgrade function in the demonstration mode of operation. The upgrade function may enable a user selection to obtain the license code, obtain the license code based on the user selection, establish a network connection to the licensing server 21a, 21b, and obtain the license code from the licensing server 21a, 21b.

In order to obtain the license code from the licensing server 21a, 21b, the barcode-reading application 24 may be configured to communicate to the licensing server 21a, 21b one of: i) a unique identification code of the mobile device 18, or ii) a user identification code identifying a controller of the mobile device 18.

The barcode-reading application 24 may include: i) an image capture function for controlling the white light source and the camera to capture an image of a barcode wherein the image of the barcode may be affected by the at least one optic system, ii) a base decoder function for decoding a barcode in a base mode of operation if an enhanced decoder mode has not been authorized, and iii) an enhanced decoder function for decoding a barcode in an enhanced mode of operation if the enhanced decoder mode has been authorized.

The enhanced decoder function may include a function of decoding a barcode that the barcode-reading application 24 is restricted from decoding in the base mode of operation. Alternatively or additionally, the enhanced decoder function may include a function of decoding multiple barcodes in sequence at a rate that is faster than a restricted rate at which the barcode-reading application 24 can decode a sequence of multiple barcodes when in the base mode of operation. Alternatively or additionally, the enhanced decoder function may include a function of decoding a quantity of barcodes of a particular symbology that exceeds a restricted quantity of barcodes of the particular symbology which the barcode-reading application 24 can decode when in the base mode of operation.

Alternatively or additionally, the enhanced decoder function may remove a demonstration restriction function under which the barcode-reading application 24 functions when in the base mode of operation, thereby making decoded data from a barcode of a particular symbology available for further processing by an application executing on the mobile device 18. The demonstration restriction function may be at least one of: i) a function which scrambles decoded data from a barcode of at least one particular symbology, ii) a function which restricts the decoded data or scrambled decoded data from a barcode of at least one particular symbology from being made available for further processing by at least one application executing on the mobile device, or iii) a function which restricts the decoded data or the scrambled decoded data from a barcode of at least one particular symbology from being displayed on a display screen of the mobile device 18.

Alternatively or additionally, the enhanced decoder function may enable at least one enhanced image processing function which improves an ability to decode an image of a barcode and is not operable when the barcode-reading application 24 operates in the base mode of operation. The enhanced decoder mode is enabled by obtaining a license code from a licensing server 21a, 21b.

The barcode-reading application 24 may be configured to subject the license code to a predetermined algorithm to determine at least one operating permission authorized by the license code. The enhanced decoder function may correspond to the at least one operating permission authorized by the license code.

The barcode-reading application 24 may be configured to obtain the license code from the licensing server 21a, 21b by communicating to the licensing server one of: i) a unique identification code of the mobile device 18, or ii) a user identification code identifying a controller of the mobile device 18.

Figure 7:
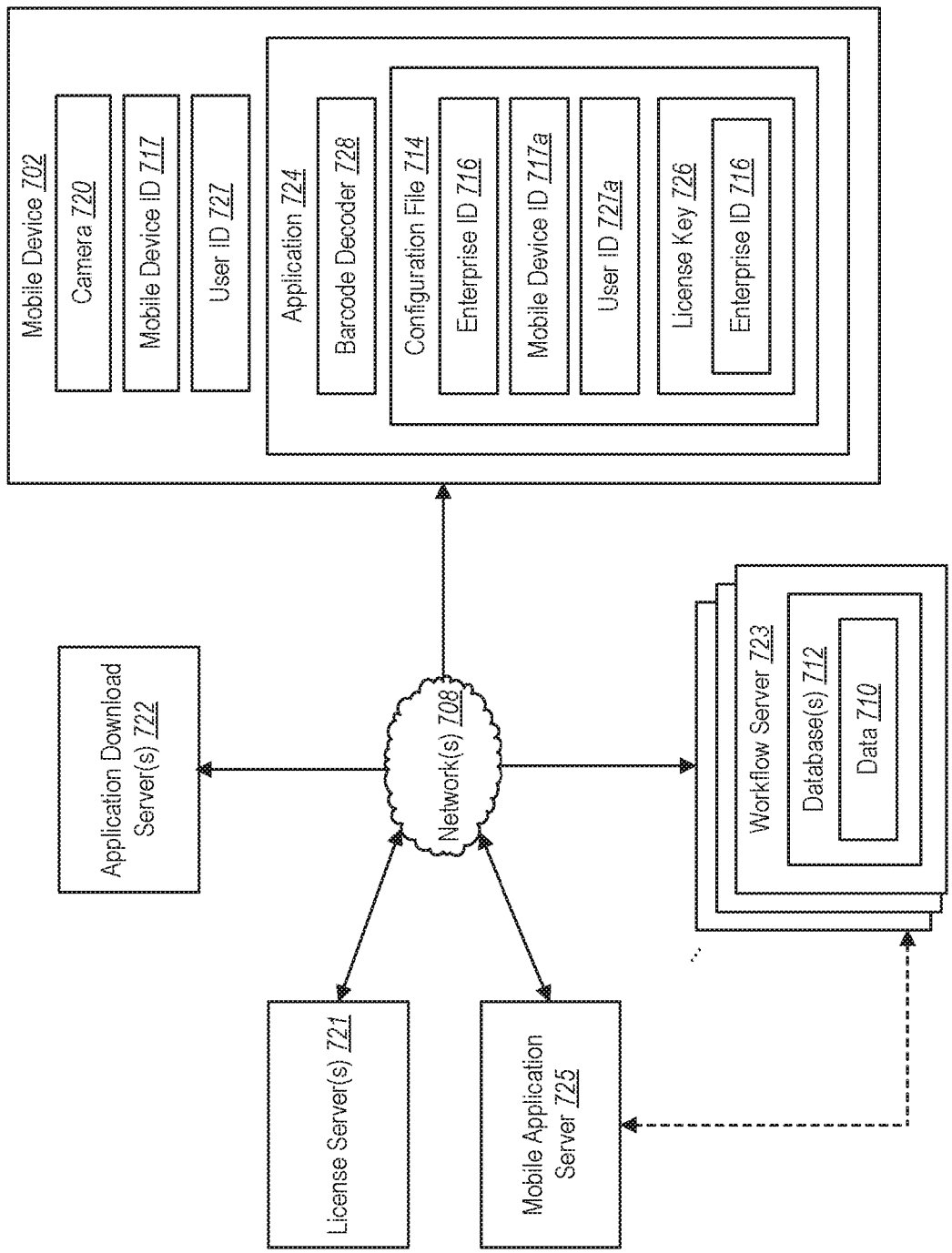
FIG. 7 illustrates an example of a system for facilitating enterprise-level licensing in accordance with the present disclosure.

Reference is now made to the system 700 that is shown in FIG. 7. As discussed above, one or more applications 724 for a mobile device 702 may be downloaded from one or more application download servers 722. The mobile device 702 may be in electronic communication with the application download server(s) 722 via one or more computer networks 708. The application download server(s) 722 may correspond to the application download servers 22a-b shown in FIG. 1. The application 724 may be the barcode reading application 24 shown in FIG. 1 or may include the barcode reading application 24.

An application 724 may be intended to be used by a variety of different individuals who may be associated with a variety of different enterprises. As used herein, the term "enterprise" refers to an organization, venture, association, group, institution, or undertaking that exists for one or more particular purposes. Some examples of enterprises include corporations, small businesses, non-profit institutions, government bodies, etc.

The system 700 includes a plurality of workflow servers 723. Data 710 associated with a particular enterprise may be stored in one or more databases 712 and accessed via one or more workflow servers 723. The workflow server(s) 723 may correspond to the workflow servers 23a-b shown in FIG. 1. Communication between the workflow server(s) 723 and an application 724 on the mobile device 702 may occur via a mobile application server 725.

It may be desirable for access to data 710 that is associated with a particular enterprise to be restricted to individuals who are associated with that enterprise. An enterprise identifier (ID) 716 may be utilized to facilitate these types of access restrictions. The enterprise ID 716 may be a value that is required for access to the enterprise's data 710 on the workflow server(s) 723.

The workflow server(s) 723 associated with a particular enterprise may implement restrictions so that the enterprise's data 710 cannot be accessed by the application 724 unless the application 724 has a configuration file 714 with the appropriate enterprise ID 716. These restrictions may be implemented in various ways. For example, any data that is sent between the workflow server(s) 723 and the mobile device 702 may be encrypted using one or more encryption keys that are derived from the enterprise ID 716 or associated with the enterprise ID 716 or associated with a session ID that is set up based on authentication using the enterprise ID 716. Thus, communication between the workflow server(s) 723 and the application 724 on the mobile device 702 may be based on the enterprise ID 716.

To enable an application 724 running on a particular mobile device 702 to access the data 710 that is associated with a particular enterprise, the application 724 may download a configuration file 714 that is associated with the enterprise. The configuration file 714 may include an enterprise ID 716 that is uniquely associated with the enterprise.

To download a configuration file 714 associated with a particular enterprise, the application 724 may connect to a workflow server 723 corresponding to that enterprise (via a mobile application server 725) and provide appropriate credentials (e.g., the enterprise ID 716, a user ID, a password). After a configuration file 714 that is associated with a particular enterprise is downloaded to the mobile device 702, the application 724 may send data 710 to and receive data 710 from the workflow server 723 corresponding to the enterprise.

To access data 710 associated with a particular enterprise, the application 724 may connect to the mobile application server 725 and communicate the enterprise ID 716 to the mobile application server 725. The mobile application server 725 may use the enterprise ID 716 to determine the workflow server 723 that is associated with the enterprise. The mobile application server 725 may then facilitate the exchange of data 710 between the application 724 and the workflow server 723.

As discussed above, a mobile device 702 may include a camera 720, such as the camera assembly 36 described previously. The application 724 may include functionality that enables the camera 720 of the mobile device 702 to be used for reading barcodes. The application 724 may also include other functionality in addition to barcode reading functionality.

Some enterprises that use the application 724 may want to use all of its functionality, including the barcode reading functionality. Other enterprises that use the application 724, however, may not have a need for the barcode reading functionality. Instead of requiring everyone who downloads the application 724 to pay for the barcode reading functionality, it may be desirable for only those enterprises that use the barcode reading functionality to pay for it. In order to make that possible, the application 724 may be configured so that its barcode reading functionality, which is represented as a barcode decoder 728 in FIG. 7, is in an inactive state when the application 724 is initially downloaded. A license key 726 may be required in order to enable use of the barcode decoder 728, i.e., to transition the barcode decoder 728 from the inactive state to an active state. The license key 726 may be the license key 26 shown in FIG. 1 or may include the license key 26.

An enterprise may purchase a license for some or all of its users to use the barcode decoder 728. When an enterprise purchases a license, a license key 726 may be created. The license key 726 may be based on the enterprise ID 716 that is associated with the enterprise (i.e., the enterprise ID 716 that facilitates access to the enterprise's data 710). For example, the license key 726 may be created using the enterprise ID 716. In some implementations, the enterprise ID 716 may be encrypted into the license key 726.

If the user of a mobile device 702 is associated with an enterprise that has purchased a license to use the barcode decoder 728, then at some point after the application 724 has been installed on the mobile device 702 the application 724 may obtain the license key 726. In some embodiments, the license key 726 may be incorporated into the configuration file 714 for the enterprise, such that the license key 726 may be obtained when the application 724 downloads the configuration file 714. Alternatively, the license key 726 may be obtained from a license server 721. The license server(s) 721 shown in FIG. 7 may correspond to the license servers 21a-b shown in FIG. 1.

Once the application 724 obtains the license key 726, the application 724 may verify that the license key 726 is based on the correct enterprise ID 716, i.e., the enterprise ID 716 that is associated with the enterprise. For example, the license key 726 may include the enterprise ID 716, and the application 724 may verify that the enterprise ID 716 within the license key 726 matches the enterprise ID 716 within the configuration file 714. Once it has been verified that the license key 726 is based on the correct enterprise ID 716, the barcode decoder 728 may be transitioned from the inactive state to the active state. Thereafter, data that is obtained from scanning barcodes may be sent to the appropriate workflow server 723 based on the enterprise ID 716.

Thus, the techniques disclosed herein facilitate enterprise-level licensing. In other words, the techniques disclosed herein enable licenses for a barcode decoder 728 to be purchased and provided for an enterprise. An application 724 that includes a barcode decoder 728 may be used by a wide variety of enterprises, some of which may be interested in using the barcode decoder 728 and some of which may not. If an enterprise purchases a license to use the barcode decoder 728, some or all of the users associated with that enterprise may be provided with a license key 726 for the barcode decoder 728 in accordance with the techniques disclosed herein. If, however, an enterprise does not purchase a license to use the barcode decoder 728, users associated with that enterprise are not provided with a license key 726 for the barcode decoder 728.

A variety of techniques may be employed to prevent a configuration file 714 from being loaded on unauthorized mobile devices and/or used by unauthorized users. In some implementations, a configuration file 714 may be created for a particular mobile device 702 such that the configuration file 714 cannot be used on other mobile devices. A mobile device 702 may be uniquely associated with a particular mobile device ID 717 (such as a serial number of the mobile device 702, a network address of the mobile device 702, or the like). The mobile device ID 717 may be stored in memory of the mobile device 702. The configuration file 714 that is created for a particular mobile device 702 may include a mobile device ID 717a that matches the mobile ID 717 of the mobile device 702. The configuration file 714 may be an encrypted file that includes an encrypted representation of the license key 726, including the enterprise ID 716, and the mobile device ID 717a. When a user of the mobile device 702 attempts to start the application 724, the application 724 may be configured to decrypt the configuration file 714 and compare the mobile device ID 717a in the configuration file 714 with the mobile device ID 717 of the mobile device 702. The application 724 may be configured so that at least some (and possibly all) of the functionality of the application 724 will not be activated unless there is a match between the mobile device ID 717a in the configuration file 714 and the mobile device ID 717 of the mobile device 702. This provides protection from the configuration file 714 being used on other devices.

Alternatively, or in addition, the configuration file 714 that is created for a particular mobile device 702 may include a user ID 727a that matches a user ID 727 that is uniquely associated with a user of the mobile device 702. The user ID 727 may be stored in memory of the mobile device 702. When a user of the mobile device 702 attempts to start the application 724, the application 724 may be configured to decrypt the configuration file 714 and compare the user ID 727a in the configuration file 714 with the user ID 727 that is stored on the mobile device 702. The application 724 may be configured so that at least some (and possibly all) of the functionality of the application 724 will not be activated unless there is a match between the user device ID 727a in the configuration file 714 and the user ID 727 that is stored on the mobile device 702.

A specific example will be discussed in relation to the system 800 shown in FIG. 8. In this example, suppose that there are two enterprises, Enterprise A and Enterprise B, that use an application 824. The application 824 may be available for download from an application download server 822. Data 810a associated with Enterprise A may be stored in one or more databases 812a and accessed via a workflow server 823a. Data 810b associated with Enterprise B may be stored in one or more databases 812b and accessed via a workflow server 823b.

It may be desirable to impose access restrictions such that only individuals associated with Enterprise A are able to access the data 810a associated with Enterprise A, and only individuals associated with Enterprise B are able to access the data 810b associated with Enterprise B. The workflow servers 823a-b may make use of IDs 816a-b associated with Enterprise A and Enterprise B to implement these access restrictions. In particular, the workflow server 823a associated with Enterprise A may implement access restrictions so that data 810a associated with Enterprise A cannot be accessed by an application 824a unless the application 824a has a configuration file 814a with a particular ID 816a that is uniquely associated with Enterprise A. Similarly, the workflow server 823b associated with Enterprise B may implement access restrictions so that data 810b associated with Enterprise B cannot be accessed by an application 824b unless the application 824b has a configuration file 814b with a particular ID 816b that is uniquely associated with Enterprise B. With these access restrictions, individuals associated with Enterprise A would not be able to access the data 810b associated with Enterprise B, and vice versa.

In some embodiments, the configuration files 814a-b may be created by the same entity that created the application 824. The configuration file 814a associated with Enterprise A may be accessed via the workflow server 823a associated with Enterprise A, and the configuration file 814b associated with Enterprise B may be accessed via the workflow server 823b associated with Enterprise B.

Figure 8:
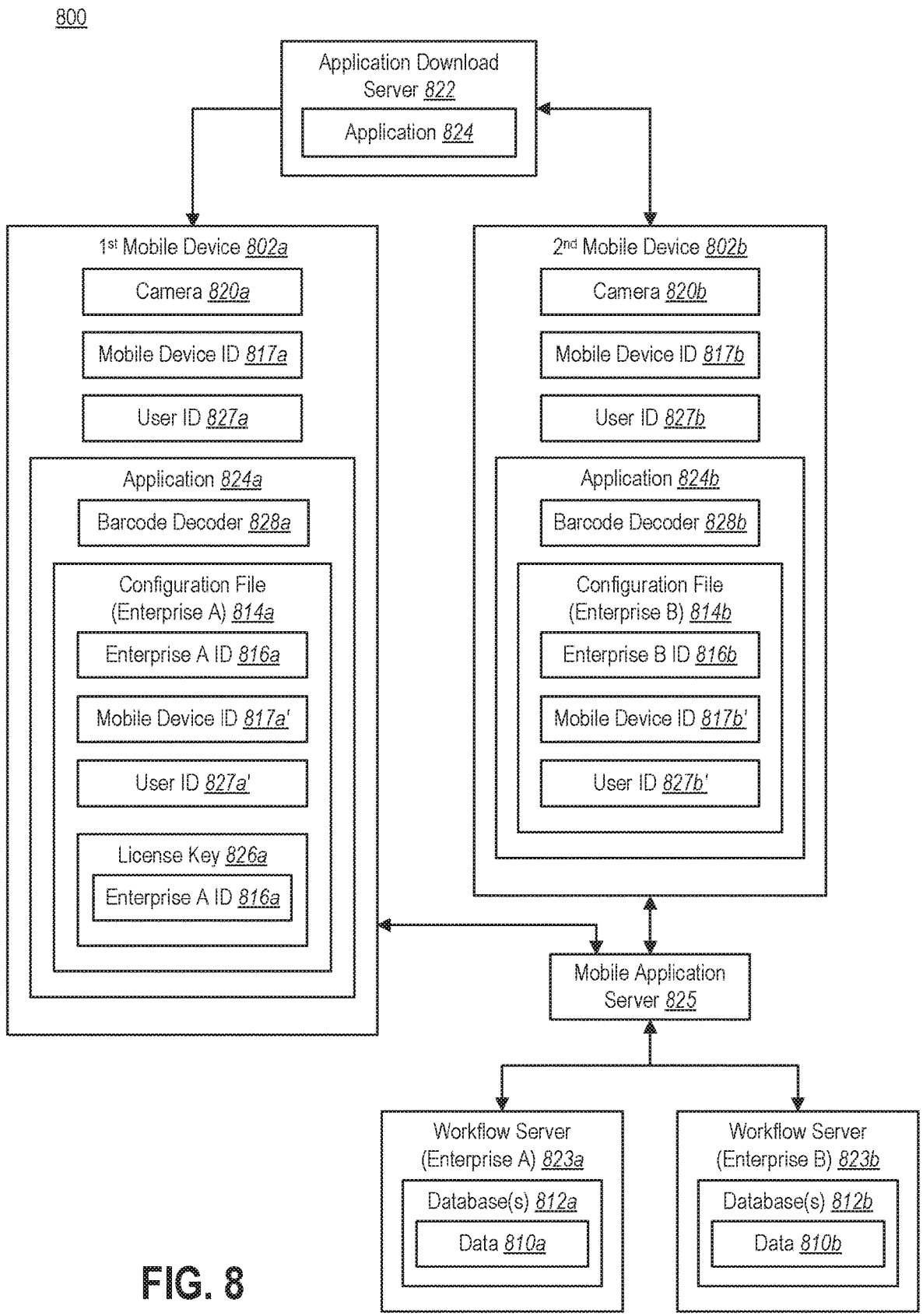
FIG. 8 illustrates an example showing how configuration files may be utilized to facilitate enterprise-level licensing for a barcode decoder that is included within a mobile device application.

The system 800 shown in FIG. 8 includes a first mobile device 802a and a second mobile device 802b. The first mobile device 802a includes a camera 820a, and the second mobile device 802b includes a camera 820b. Suppose that the first mobile device 802a is used by someone who is associated with Enterprise A, and that the second mobile device 802b is used by someone who is associated with Enterprise B. The user of the first mobile device 802a may download a copy of the application 824a (e.g., from an application download server 722), and the user of the second mobile device 802b may also download a copy of the application 824b. To facilitate access to the data 810a that is associated with Enterprise A, the user of the first mobile device 802a may download a configuration file 814a from the workflow server 823a associated with Enterprise A. The configuration file 814a may include a mobile device ID 817a' that matches a mobile device ID 817a uniquely associated with the first mobile device 802a. Alternatively, or in addition, the configuration file 814a may include a user ID 827a' that matches a user ID 827a uniquely associated with a user of the first mobile device 802a. Similarly, to facilitate access to the data 810b that is associated with Enterprise B, the user of the second mobile device 802b may download a configuration file 814b associated with Enterprise B from the workflow server 823b associated with Enterprise B. The configuration file 814b may include a mobile device ID 817b' that matches a mobile device ID 817b uniquely associated with the second mobile device 802b. Alternatively, or in addition, the configuration file 814b may include a user ID 827b' that matches a user ID 827b uniquely associated with a user of the second mobile device 802b. As discussed above, interactions between the applications 824a-b and the workflow servers 823a-b may occur via a mobile application server 825.

When the users of the first and second mobile devices 802a-b download their respective copies of the application 824a-b, the barcode decoder 828a-b may initially be in an inactive state. Suppose that Enterprise A has purchased a license to use the barcode decoder 828a, but Enterprise B has not. Because Enterprise A has purchased a license, at some point after the first mobile device 802a has downloaded the application 824a it may obtain a license key 826a for the barcode decoder 828a. For example, as shown in FIG. 8, the configuration file 814a that is created for the first mobile device 802a may include the license key 826a. When the user of the first mobile device 802a attempts to use the barcode decoder 828a, the application 824a may verify that the mobile device ID 817a' in the configuration file 814a matches the mobile device ID 817a for the first mobile device 802a. Alternatively, or in addition, the application 824a may verify that the user ID 827a' in the configuration file 814a matches the user ID 827a for the user of the first mobile device 802a. The application 824a may also verify that the license key 826a is based on the enterprise ID 816a associated with Enterprise A.

Once the application 824a verifies that the mobile device ID 817a' in the configuration file 814a matches the mobile device ID 817a for the first mobile device 802a (and/or that the user ID 827a' in the configuration file 814a matches the user ID 827a for the user of the first mobile device 802a) and also that the license key 826a is based on the enterprise ID 816a associated with Enterprise A, the barcode decoder 828a may be transitioned from the inactive state to the active state. In the active state, the full functionality of the barcode decoder 828a may be available. Because Enterprise B has not purchased a license to use the barcode decoder 828b, however, the configuration file 814b associated with Enterprise B does not include a license key. Thus, the barcode decoder 828b may remain in the inactive state on the second mobile device 802b, such that the user of the second mobile device 802b is not able to use the barcode decoder 828b.

When the first mobile device 802a is used to read a barcode, the decoded data that is created by the barcode decoder 828a may be sent to the workflow server 823a that is associated with Enterprise A. The decoded data may be associated with the enterprise ID 816a, and the enterprise ID 816a may indicate to the mobile application server 825 which workflow server 823*a* (of the available workflow servers 823*a-b*) should receive the decoded data.

Figure 9:
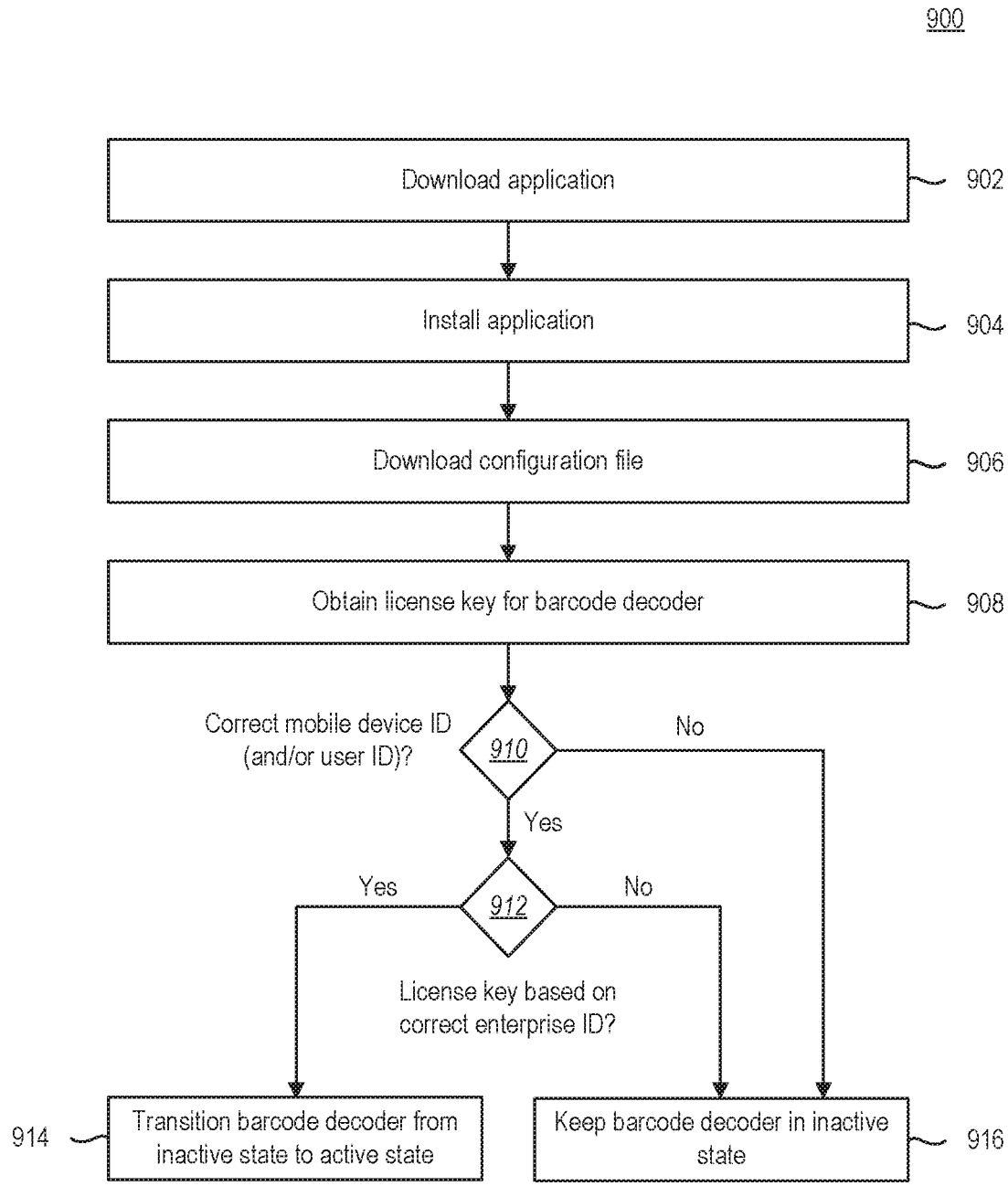
FIG. 9 illustrates an example of a method that may be performed by a mobile device to implement enterprise-level licensing in accordance with the present disclosure.

FIG. 9 illustrates an example of a method 900 that may be performed by a mobile device 702 to implement enterprise-level licensing in accordance with the present disclosure. The method 900 will be discussed in relation to the system 700 shown in FIG. 7.

As discussed above, an application 724 may be intended to be used by a variety of different individuals who may be associated with a variety of different enterprises. Someone who is associated with a particular enterprise may use his/her mobile device 702 to download 902 the application 724 from an application download server 722 and install 904 the application 724 on the mobile device 702. The application 724 may include a barcode decoder 728. When the application 724 is initially installed, the barcode decoder 728 may be in an inactive state.

In order to access the data 710 that is associated with the enterprise, the application 724 may download 906 a configuration file 714. The configuration file 714 may be an encrypted file that is downloaded from a workflow server 723 associated with the enterprise. The configuration file 714 may include an enterprise ID 716 that is uniquely associated with the enterprise. The configuration file 714 may also include a mobile device ID 717*a* that matches a mobile ID 717 for the mobile device 702 (and/or a user ID 727*a* that matches a user ID 727 for a user of the mobile device 702). The mobile device ID 717*a* (and/or the user ID 727*a*) may be used to prevent the configuration file 714 from being used by unauthorized mobile devices.

If the enterprise wants its users to be able to use the barcode decoder 728, the enterprise may purchase a license to use the barcode decoder 728. If the enterprise has purchased a license, the application 724 may obtain 908 the license key 726 for the barcode decoder 728. For example, the license key 726 may be incorporated into the configuration file 714 for the enterprise, such that the license key 726 may be obtained from the workflow server 723 when the application 724 downloads the configuration file 714. In some implementations, the enterprise ID 716 may be encrypted into the license key 726.

At some point after the application 724 has obtained 908 the license key 726, the application 724 may determine 910 whether the mobile device ID 717*a* in the configuration file 714 matches the mobile device ID 717 for the mobile device 702. Alternatively, or in addition, the application 724 may determine 910 whether the user ID 727*a* in the configuration file 714 matches the user ID 727 for the user of the mobile device 702.

If it is determined 910 that the mobile device ID 717*a* in the configuration file 714 does not match the mobile device ID 717 for the mobile device 702 (and/or that the user ID 727*a* in the configuration file 714 does not match the user ID 727 for the user of the mobile device 702), the barcode decoder 728 may be kept 916 in the inactive state. Other actions may also be taken, such as deactivating at least some additional functionality (and possibly all functionality) of the application 724.

If, however, it is determined 910 that the mobile device ID 717*a* in the configuration file 714 matches the mobile device ID 717 for the mobile device 702 (and/or that the user ID 727*a* in the configuration file 714 matches the user ID 727 for the user of the mobile device 702), the application 724 may then determine 912 whether the license key 726 is based on the correct enterprise ID 716, i.e., the enterprise ID 716 that is associated with the appropriate enterprise and that facilitates access to the enterprise's data 710. For example, the license key 726 may include the enterprise ID 716, and the application 724 may determine whether the enterprise ID 716 within the license key 726 matches the enterprise ID 716 within the configuration file 714. If the application 724 determines 912 that the license key 726 is based on the correct enterprise ID 716, the application 724 may transition 914 the barcode decoder 728 from the inactive state to the active state. If, however, the application 724 determines 912 that the license key 726 is not based on the correct enterprise ID 716, the barcode decoder 728 may be kept 916 in the inactive state. In other words, the application 724 may transition the barcode decoder 728 from the inactive state to the active state conditional upon verifying that the configuration file 714 is associated with the correct mobile device 702 (and/or the correct user) and also upon verifying that the license key 726 is based on the correct enterprise ID 716.

Figure 10:
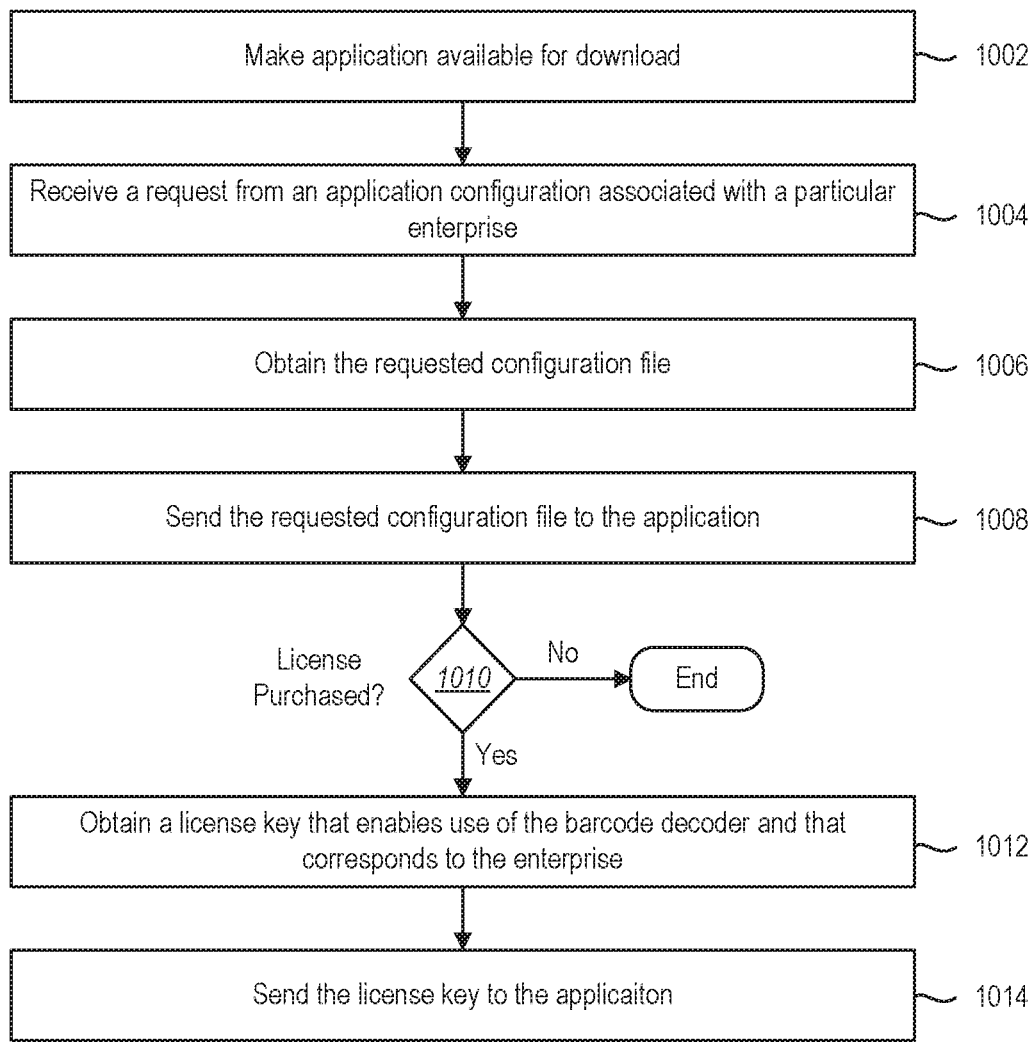
FIG. 10 illustrates an example of a method that may be performed by an application vendor to implement enterprise-level licensing in accordance with the present disclosure.

FIG. 10 illustrates another example of a method 1000 for enterprise-level licensing in accordance with the present disclosure. The method 1000 will be discussed in relation to the system 700 shown in FIG. 7. The method 1000 may be performed by an entity that creates and/or distributes an application 724 that is intended to be used by a variety of different individuals who may be associated with a variety of different enterprises. In the discussion that follows, such an entity will be referred to as an application vendor.

The application vendor may make 1002 the application 724 available to be downloaded. In some embodiments, the application 724 may be made available so that any member of the general public may download the application 724 (e.g., via one or more application download servers 722).

When a user associated with a particular enterprise wants to access the data 710 that is associated with the enterprise, the user may (via the application 724 on his/her mobile device 702) request a configuration file 714 that is associated with the enterprise. A workflow server 723 may receive 1004 the request from the application 724 (via a mobile application server 725). The request may include an enterprise ID 716 as well as user credentials such as a user ID 727, a password, etc. The request may also include a mobile device ID 717 for the mobile device 702.

If the user credentials are authenticated, the workflow server 723 may obtain 1006 the requested configuration file 714. For example, the workflow server 723 may create the configuration file 714 or request the configuration file 714 from another entity that creates the configuration file 714. The configuration file 714 may include the enterprise ID 716 that is uniquely associated with the enterprise. The configuration file 714 may also include the mobile device ID 717*a* and/or the user ID 727*a* (to prevent the configuration file 714 from being used on an unauthorized mobile device, as discussed above). Once the configuration file 714 has been obtained 1006, the workflow server 723 may send 1008 the configuration file 714 to the application 724.

At some point, a determination may be made 1010 about whether the enterprise has purchased a license to use the barcode decoder 728. In some embodiments, the enterprise may purchase a license to use the barcode decoder 728 directly from the application vendor. Alternatively, the enterprise may purchase a license to use the barcode decoder 728 from a supplier of the barcode decoder 728. In such embodiments, the application vendor may contact the supplier of the barcode decoder 728 to confirm that the enterprise has purchased a license to use the barcode decoder 728.

If it is determined 1010 that the enterprise has purchased a license to use the barcode decoder 728, then the application vendor may obtain 1012 a license key 726 that enables use of the barcode decoder 728 and that corresponds to the enterprise (e.g., a license key 726 that is based on the enterprise ID 716 that facilitates access to the enterprise's data 710). In some embodiments, the application vendor may receive the license key 726 from a supplier of the barcode decoder 728. Alternatively, the application vendor may create the license key 726 itself.

Once the license key 726 has been obtained 1012, the application vendor may send 1014 the license key 726 to the application 724. In some embodiments, the application vendor may incorporate the license key 726 into the configuration file 714 for the enterprise, such that the license key 726 is sent to the application 724 along with the configuration file 714. Alternatively, the license key 726 may be sent to the application 724 separately from the configuration file 714 (e.g., via a license server 721, which may be distinct from the workflow server 723).

Figure 11:
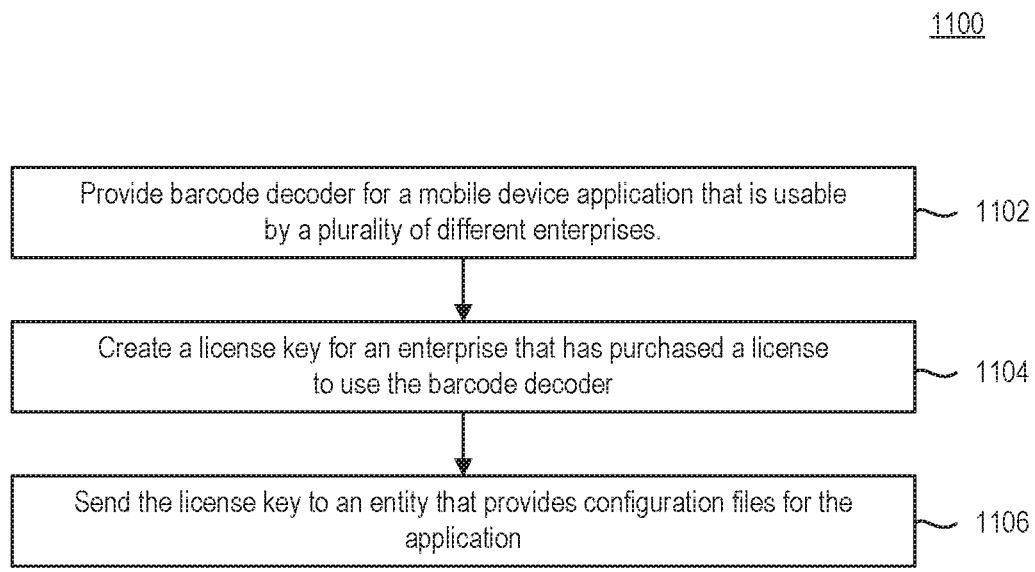
FIG. 11 illustrates an example of a method that may be performed by a supplier of a barcode decoder to implement enterprise-level licensing in accordance with the present disclosure.

FIG. 11 illustrates another example of a method 1100 for enterprise-level licensing in accordance with the present disclosure. The method 1100 will be discussed in relation to the system 700 shown in FIG. 7. The method 1100 may be performed by a supplier of a barcode decoder 728.

In accordance with the method 1100, a barcode decoder 728 may be provided 1102 for a mobile device application 724 that is usable by a variety of different individuals who may be associated with a variety of different enterprises. When an enterprise purchases a license to use the barcode decoder 728, a license key 726 may be created 1104 for the enterprise. The license key 726 may enable use of the barcode decoder 728 and may be associated with the enterprise. The license key 726 may be based on the enterprise ID 716 that is associated with the enterprise (i.e., the enterprise ID 716 that facilitates access to the enterprise's data 710). For example, the enterprise ID 716 may be encrypted into the license key 726.

The license key 726 may be sent 1106 to an entity (e.g., an application vendor) that provides configuration files 714 for the application 724. As discussed above, such an entity may incorporate the license key 726 into any configuration files 714 that are created for mobile devices 702 associated with the enterprise.

Figure 12:
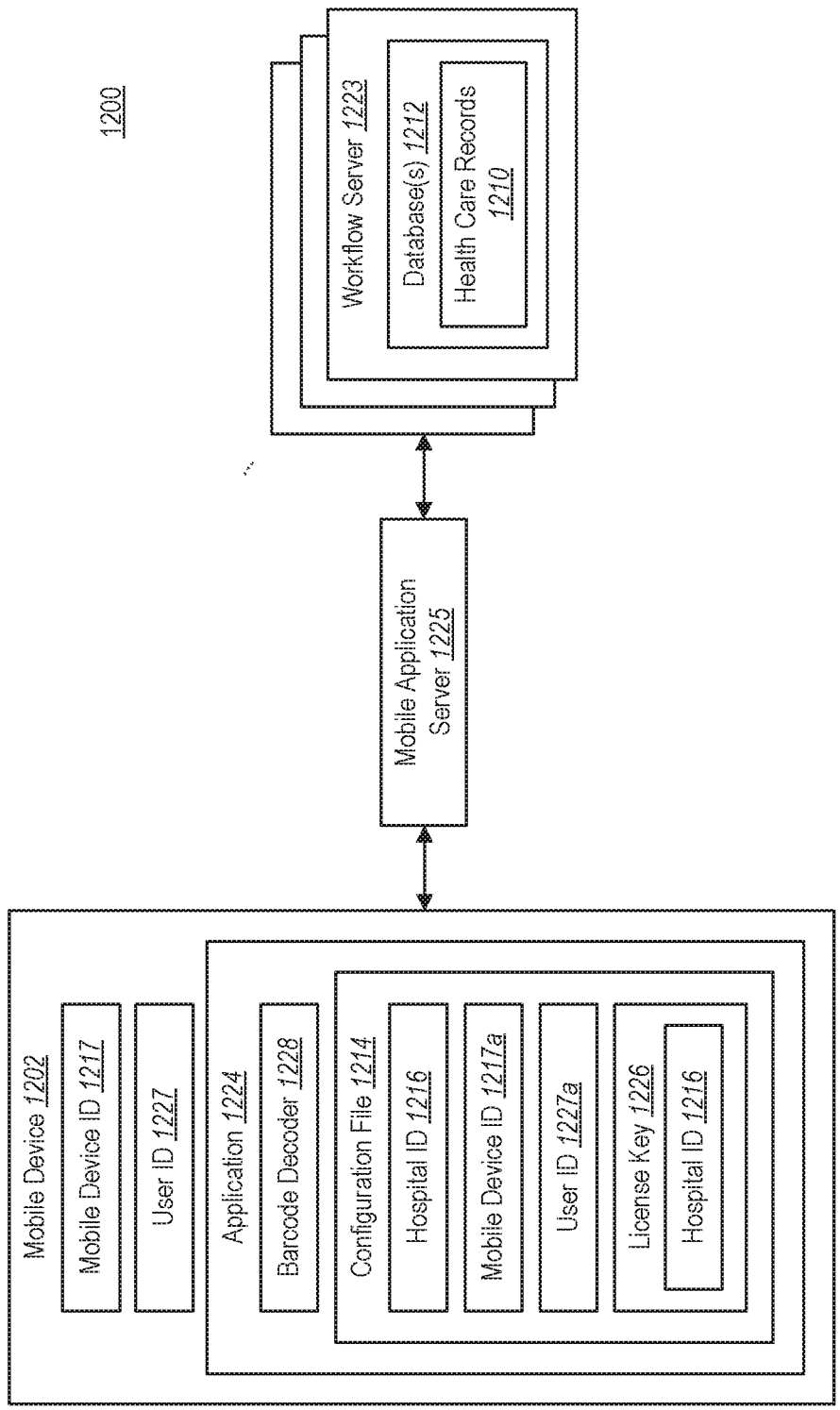
FIG. 12 illustrates an example of a system in which the techniques disclosed herein may be utilized in connection with hospitals.

As discussed above, the techniques disclosed herein facilitate enterprise-level licensing. One specific type of enterprise with which the techniques disclosed herein may be utilized is a hospital or other type of medical institution or facility. FIG. 12 illustrates an example of a system 1200 in which the techniques disclosed herein may be utilized in connection with hospitals.

A hospital information system (HIS) vendor may maintain health care records 1210 for a plurality of different medical facilities, such as hospitals. Health care records 1210 associated with a particular hospital may be stored in one or more databases 1212 and accessed via a workflow server 1223. The HIS vendor may create an application 1224 for the purpose of enabling a mobile device 1202 to retrieve and/or generate data related to health care records 1210.

To enable an application 1224 running on a particular mobile device 1202 to be able to access the health care records 1210 that are associated with a particular hospital, a configuration file 1214 may be created for the mobile device 1202 and downloaded to the mobile device 1202. For example, the user of the mobile device 1202 may use the application 1224 to request health care records 1210 associated with a particular hospital. The request may include information identifying the hospital (e.g., a hospital ID 1216), the mobile device 1202 (e.g., the mobile device ID 1217), and appropriate user credentials (e.g., a user ID 1227 and a password). A configuration file 1214 may be created and sent to the application 1224 in response to the request. The configuration file 1214 may include a hospital ID 1216 that is uniquely associated with the hospital. The hospital ID 1216 may be assigned by the HIS vendor. In addition, to prevent the configuration file 1214 from being used on unauthorized mobile devices, the configuration file 1214 may include a mobile device ID 1217a that matches the mobile device ID 1217 associated with the mobile device 1202. Alternatively, or in addition, the configuration file 1214 may include a user ID 1227a that matches the user ID 1227 associated with the user of the mobile device 1202.

The configuration file 1214 may be downloaded from a workflow server 1223. The workflow server 1223 may be provided by the HIS vendor. The HIS vendor may provide a plurality of different workflow servers 1223 associated with different hospitals.

The application 1224 may include a barcode decoder 1228 that is in an inactive state when the application 1224 is initially downloaded. A license key 1226 may be required in order to transition the barcode decoder 1228 from the inactive state to an active state. A hospital may purchase a license key 1226 for some or all of its users. The license key 1226 may be based on the hospital ID 1216 that is associated with the hospital (i.e., the hospital ID 1216 that facilitates access to health care records 1210 that are associated with the hospital).

If the user of a mobile device 1202 is associated with a hospital that has purchased a license to use the barcode decoder 1228, then at some point after the application 1224 has been installed on the mobile device 1202 the application 1224 may obtain the license key 1226. In some embodiments, the license key 1226 may be incorporated into the configuration file 1214 for the hospital, such that the license key 1226 may be obtained when the application 1224 downloads the configuration file 1214 from the workflow server 1223.

Once the application 1224 obtains the license key 1226, the application 1224 may verify that the configuration file 1214 is authorized (e.g., by verifying that the mobile device ID 1217a in the configuration file 1214 matches the mobile device ID 1217 for the mobile device 1202, and/or that the user ID 1227a in the configuration file 1214 matches the user ID 1227 for the user of the mobile device 1202). The application 1224 may also verify that the license key 1226 is based on the correct hospital ID 1216. Once it has been verified that the configuration file 1214 is authorized and that the license key 1226 is based on the correct hospital ID 1216, the barcode decoder 1228 may be transitioned from the inactive state to the active state. Thereafter, data that is obtained from scanning barcodes may be sent to the appropriate workflow server 1223, via the mobile application server 1225, based on the hospital ID 1216.

The mobile devices 702, 802a-b, 1202 that were discussed above in connection with the systems 700, 800, 1200 shown in FIGS. 7, 8, and 12, respectively, may include some or all of the features of the mobile device 18 that was discussed above in connection with FIG. 2. For example, the mobile devices 702, 802a-b, 1202 may include one or more processors 44 and memory 46 in electronic communication with the one or more processors 44. Instructions (including one or more mobile device applications 724, 824a-b, 1224 as well as other instructions) may be stored in the memory 46 and executed by the one or more processors 44 to implement the functionality described herein.

The various servers that have been described herein (e.g., the workflow servers 723, 823a-b, 1223, mobile application servers 725, 825, 1225, application download server(s) 722, license server(s) 721) may be logical entities. In some embodiments, some or all of these servers may be implemented using the same hardware. In other embodiments, some or all of these servers may be implemented using different hardware.

The techniques described herein may be implemented in hardware, software, firmware, or any combination thereof, unless specifically described as being implemented in a specific manner. Any features described as modules, components, or the like may also be implemented together in an integrated logic device or separately as discrete but interoperable logic devices. If implemented in software, the techniques may be realized at least in part by a non-transitory processor-readable storage medium comprising instructions that, when executed by at least one processor, perform one or more of the methods described herein. The instructions may be organized into routines, programs, objects, components, data structures, etc., which may perform particular tasks and/or implement particular data types, and which may be combined or distributed as desired in various embodiments.

The steps and/or actions of the methods described herein may be interchanged with one another without departing from the scope of the claims. In other words, unless a specific order of steps or actions is required for proper operation of the method that is being described, the order and/or use of specific steps and/or actions may be modified without departing from the scope of the claims.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element or feature described in relation to an embodiment herein may be combinable with any element or feature of any other embodiment described herein, where compatible.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A mobile device, comprising:
   one or more processors;
   memory in electronic communication with the one or more processors; and
   an application stored in the memory of the mobile device, the application comprising a barcode decoder, the application being executable by the one or more processors to:
   download a configuration file from a workflow server, wherein the configuration file comprises an enterprise identifier that is uniquely associated with an enterprise, and wherein communication between the application and the workflow server occurs via a mobile application server and is based on the enterprise identifier;
   obtain a license key for the barcode decoder, the license key being based on the enterprise identifier; and
   transition the barcode decoder from an inactive state to an active state conditional upon verifying that the license key is based on the enterprise identifier.

2. The mobile device of claim 1, wherein:
   the memory further comprises instructions that are executable by the one or more processors to download the application from an application download server and install the application; and
   the barcode decoder is in the inactive state when the application is installed.

3. The mobile device of claim 1, wherein:
   the license key comprises the enterprise identifier; and
   verifying that the license key is based on the enterprise identifier comprises verifying that the enterprise identifier within the license key matches the enterprise identifier within the configuration file.

4. The mobile device of claim 1, wherein the license key is obtained from the workflow server.

5. The mobile device of claim 4, wherein the configuration file comprises the license key.

6. The mobile device of claim 1, wherein the license key is obtained from a license server that is distinct from the workflow server.

7. The mobile device of claim 1, wherein the application comprises barcode reading functionality and other functionality in addition to the barcode reading functionality.

8. The mobile device of claim 1, wherein:
   the workflow server is managed by a hospital information system (HIS) vendor;
   the enterprise comprises a hospital; and
   the enterprise identifier comprises a hospital identifier.

9. The mobile device of claim 8, wherein the HIS vendor assigns the hospital identifier to the hospital.

10. A method for enterprise-level licensing, the method being implemented by a hospital information system (HIS) vendor, the method comprising:
    sending a configuration file to an application running on a mobile device, wherein a user of the mobile device is associated with a hospital, wherein the configuration file comprises a hospital identifier that is uniquely associated with the hospital, and wherein the configuration file is sent to the application in response to receiving a request for access to health care records maintained by the HIS vendor and receiving information identifying the hospital;
    obtaining a license key for the hospital, the license key enabling use of a barcode decoder within the application, the license key being based on the hospital identifier; and
    sending the license key to the application.

11. The method of claim 10, further comprising creating the configuration file, wherein the configuration file comprises at least one of:
    a mobile device identifier that is uniquely associated with the mobile device; or
    a user identifier that is uniquely associated with a user of the mobile device.

12. The method of claim 10, further comprising determining whether the enterprise has purchased a license to use the barcode decoder, wherein the license key is sent to the application conditional upon determining that the enterprise has purchased the license.

13. The method of claim 10, wherein obtaining the license key comprises receiving the license key from a supplier of the barcode decoder.

14. The method of claim 10, wherein the configuration file comprises the license key.

15. A system for enterprise-level licensing, comprising:
a workflow server comprising memory including a database that includes enterprise data associated with an enterprise, wherein the workflow server is configured to implement access restrictions so that the enterprise data cannot be accessed by a mobile device application unless the mobile device application has a configuration file comprising an enterprise identifier that is uniquely associated with the enterprise;
a mobile application server that facilitates communication between the mobile device application and the workflow server, wherein the communication between the mobile device application and the workflow server is based on the enterprise identifier; and
a license server that is configured to provide a license key to the mobile device, wherein the license key is based on the enterprise identifier, and wherein the license key is required to transition a barcode decoder that is part of the mobile device application from an inactive state to an active state.

16. The system of claim 15, wherein the communication between the mobile device application and the workflow server is encrypted using an encryption key that is based at least in part on the enterprise identifier.

17. The system of claim 15, wherein:
the license server is part of the workflow server;
the workflow server is configured to download the configuration file to the mobile device in response to the mobile device providing credentials verifying that the mobile device is authorized to access the enterprise data; and
the license key is incorporated into the configuration file.

18. The system of claim 15, wherein the license server is separate from the workflow server.

19. The system of claim 15, wherein the enterprise identifier is encrypted into the license key.

20. The system of claim 15, wherein the system comprises a plurality of workflow servers, and wherein the mobile application server is configured to:
receive the enterprise identifier from the mobile device application; and
determine which of the plurality of workflow servers is associated with the enterprise based at least in part on the enterprise identifier.

* * * * *